US011780990B2

(12) United States Patent
Ishima et al.

(10) Patent No.: US 11,780,990 B2
(45) Date of Patent: Oct. 10, 2023

(54) PARTICULATE ULTRAVIOLET ABSORBER AND RESIN COMPOSITION

(71) Applicant: ADEKA CORPORATION, Tokyo (JP)

(72) Inventors: Yosuke Ishima, Saitama (JP); Kohei Omori, Saitama (JP)

(73) Assignee: ADEKA CORPORATION, Tokyo (JP)

( * ) Notice: Subject to any disclaimer, the term of this patent is extended or adjusted under 35 U.S.C. 154(b) by 364 days.

(21) Appl. No.: 17/043,074

(22) PCT Filed: Mar. 25, 2019

(86) PCT No.: PCT/JP2019/012517
§ 371 (c)(1),
(2) Date: Sep. 29, 2020

(87) PCT Pub. No.: WO2019/188987
PCT Pub. Date: Oct. 3, 2019

(65) Prior Publication Data
US 2021/0017360 A1 Jan. 21, 2021

(30) Foreign Application Priority Data

Mar. 30, 2018 (JP) ................................. 2018-067807
Mar. 30, 2018 (JP) ................................. 2018-067830

(51) Int. Cl.
C08K 5/3492 (2006.01)
(52) U.S. Cl.
CPC ................................. C08K 5/3492 (2013.01)

(58) Field of Classification Search
CPC ... C08K 5/3492; C07D 251/24; C08L 101/00; C09D 5/32; C09D 7/48; C09D 7/63; C09K 3/00
See application file for complete search history.

(56) References Cited

U.S. PATENT DOCUMENTS

| 6,111,103 A * | 8/2000 | Ehlis ................... C07D 405/12 |
| | | 544/219 |
| 6,225,375 B1 | 5/2001 | Thibaut et al. |
| 6,740,694 B2 | 5/2004 | Thibaut et al. |

(Continued)

FOREIGN PATENT DOCUMENTS

| JP | 11-71356 A | 3/1999 |
| JP | 2001-55395 A | 2/2001 |

(Continued)

OTHER PUBLICATIONS

Thummler et al., An Introduction to Powder Metallurgy, 1993, p. 65-108.*
Carson et al., Bulk Properties of Powders, 1998, p. 287-301.*

Primary Examiner — Robert S Jones, Jr.
Assistant Examiner — Jiangtian Xu
(74) Attorney, Agent, or Firm — GREENBLUM & BERNSTEIN, P.L.C.

(57) ABSTRACT

A particulate ultraviolet absorber is provided and includes a predetermined triazine-based compound, in which in a case where a loose bulk density is denoted by D1 and a tight bulk density is denoted by D2, which are measured under predetermined measurement condition, compressibility represented by $[(D2-D1)/D2] \times 100$ is 5.0% or more and 40% or less.

14 Claims, 3 Drawing Sheets

(56) References Cited

U.S. PATENT DOCUMENTS

| | | | |
|---|---|---|---|
| 7,311,897 | B2 | 12/2007 | Ehlis et al. |
| 7,326,744 | B2 | 2/2008 | Fukuoka et al. |
| 8,044,123 | B2 | 10/2011 | Aniasaki et al. |
| 8,105,668 | B2 | 1/2012 | Brunner et al. |
| 8,518,503 | B2 | 8/2013 | Brunner et al. |
| 9,969,702 | B2 | 5/2018 | Ishima et al. |
| 2001/0023269 | A1 | 9/2001 | Thibaut et al. |
| 2004/0191191 | A1 | 9/2004 | Ehlis et al. |
| 2004/0242733 | A1 | 12/2004 | Fukuoka et al. |
| 2010/0324181 | A1 | 12/2010 | Aniasaki et al. |
| 2011/0027509 | A1 | 2/2011 | Brunner et al. |
| 2011/0272648 | A1* | 11/2011 | Fukushima .......... C08K 5/3492 252/589 |
| 2012/0094565 | A1 | 4/2012 | Brunner et al. |
| 2017/0327475 | A1 | 11/2017 | Ishima et al. |
| 2019/0016661 | A1 | 1/2019 | Inoue et al. |

FOREIGN PATENT DOCUMENTS

| | | |
|---|---|---|
| JP | 2001-323251 A | 11/2001 |
| JP | 2001-526711 A | 12/2001 |
| JP | 2002-193951 A | 7/2002 |
| JP | 2003-137874 A | 5/2003 |
| JP | 2004-51576 A | 2/2004 |
| JP | 2006-523197 A | 10/2006 |
| JP | 2010-202521 A | 9/2010 |
| JP | 2011-6517 A | 1/2011 |
| JP | 2011-505400 A | 2/2011 |
| WO | 2016/093108 A1 | 6/2016 |
| WO | 2017/154947 A1 | 9/2017 |

* cited by examiner

PARTICULATE ULTRAVIOLET ABSORBER AND RESIN COMPOSITION

TECHNICAL FIELD

The present invention relates to a particulate ultraviolet absorber and a resin composition.

BACKGROUND ART

So far, various developments have been made in ultraviolet absorbers. As this kind of technology, for example, the technology described in Patent Document 1 is known. Patent Document 1 describes the use of a triazine-based compound as an ultraviolet absorber, which is obtained by crystallization (paragraph 0102 in Patent Document 1 and the like).

RELATED DOCUMENT

Patent Document

[Patent Document 1] Japanese Unexamined Patent Publication No. 2011-6517

SUMMARY OF THE INVENTION

However, as a result of the study by the inventors of the present invention, it was found that the ultraviolet absorber described in Patent Document 1 has room for improvement in terms of powder characteristics.

As a result of further study, the inventors of the present invention have found that the powder characteristics of a particulate ultraviolet absorber containing a triazine-based compound can be appropriately controlled by using the compressibility as an index. Further intensive studies based on such findings have revealed that the powder characteristics in the above-mentioned particulate ultraviolet absorber are improved by setting the compressibility within a predetermined numerical range and have completed the present invention.

The present invention provides, a particulate ultraviolet absorber including a triazine-based compound, in which in a case where a loose bulk density is denoted by D1 and a tight bulk density is denoted by D2, which are measured under the following measurement condition, compressibility represented by $[(D2-D1)/D2] \times 100$ is 5.0% or more and 40% or less.

(Measurement Condition)

A predetermined container is filled with the particulate ultraviolet absorber, the particulate ultraviolet absorber is leveled off without tapping, and then the loose bulk density (g/cm$^3$) of the particulate ultraviolet absorber in the container is measured.

In addition, a predetermined container is filled with the particulate ultraviolet absorber, the particulate ultraviolet absorber is tapped from a height of 18 mm under a condition of 180 times of tapping, leveled off, and then the tight bulk density (g/cm$^3$) of the particulate ultraviolet absorber in the container is measured.

In addition, according to the present invention, a resin composition containing the particulate ultraviolet absorber is provided.

According to the present invention, a particulate ultraviolet absorber having excellent powder characteristics and a resin composition using the particulate ultraviolet absorber are provided.

BRIEF DESCRIPTION OF THE DRAWINGS

The above-described and other objects, characteristics, and advantages will be more clear from the preferred embodiments and the accompanying drawings described below.

DESCRIPTION OF EMBODIMENTS

Figure 1:
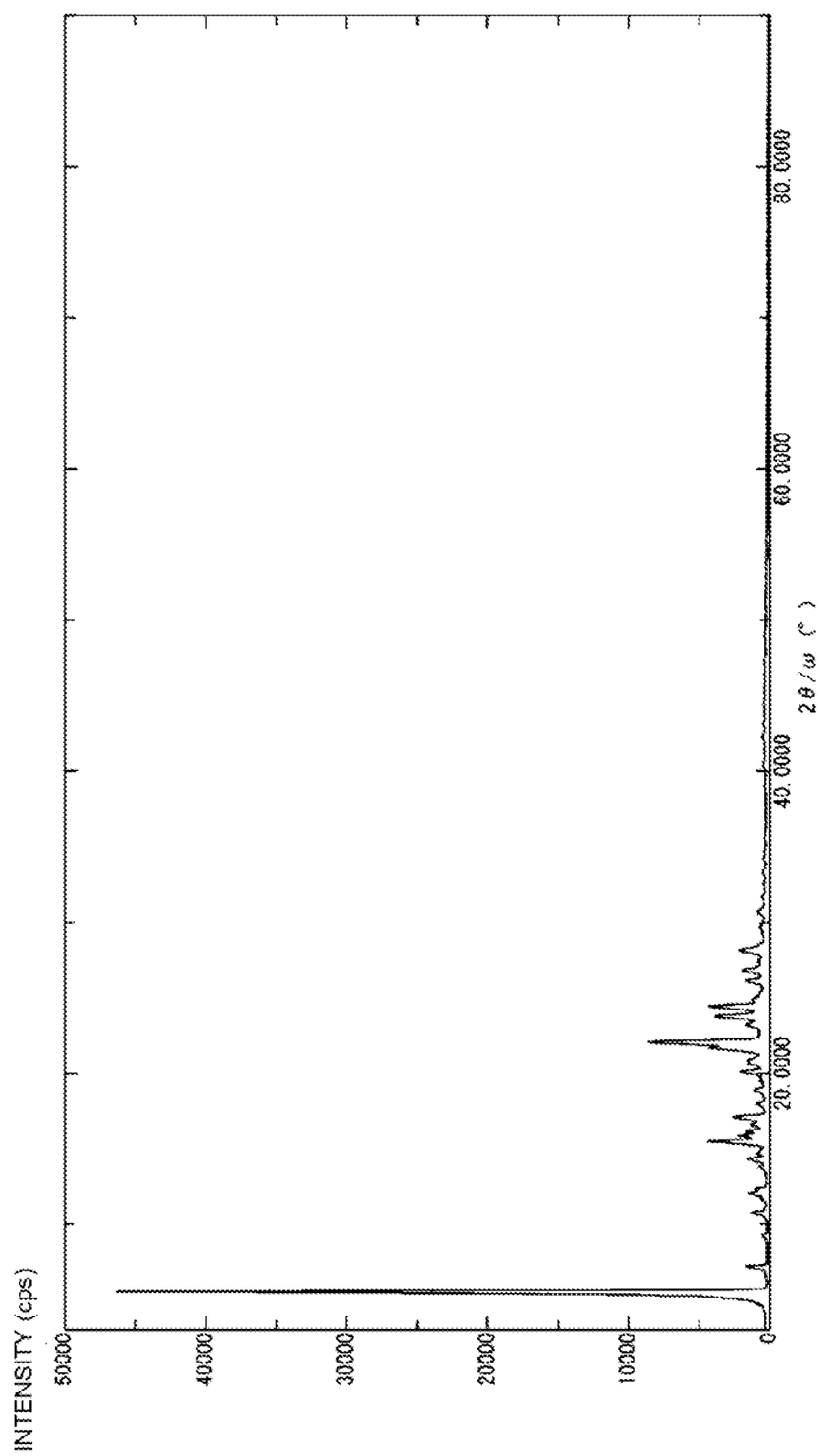
FIG. 1 is an X-ray diffraction pattern of a particulate ultraviolet absorber of Example 1.

A particulate ultraviolet absorber of the present embodiment contains a triazine-based compound.

The triazine-based compound preferably contains a compound represented by General Formula (I). These compounds may be used alone or in the combination of two or more thereof.

The particulate ultraviolet absorber may be composed only of the following triazine-based compound.

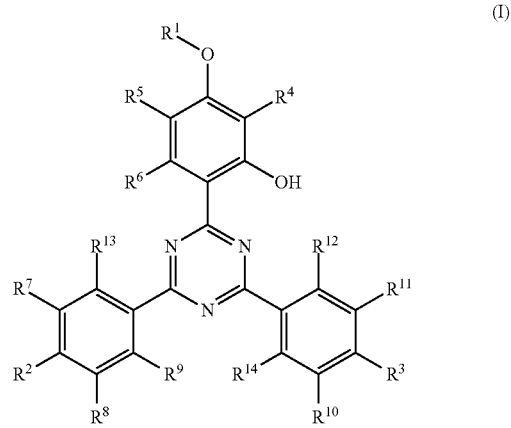

(I)

In General Formula (I), $R^1$ represents a linear or branched alkyl group having 1 to 20 carbon atoms, a cycloalkyl group having 3 to 20 carbon atoms, an aryl group having 6 to 20 carbon atoms, an alkylaryl group having 7 to 20 carbon atoms, an arylalkyl group having 7 to 20 carbon atoms, or an alkenyl group having 2 to 8 carbon atoms, which is substituted or unsubstituted, or a substituent represented by General Formula (II), $R^2$ and $R^3$ each independently represent a hydrogen atom, a linear or branched alkyl group having 1 to 20 carbon atoms, which is substituted or unsubstituted, or —O—R, where R represents a linear or branched alkyl group having 1 to 20 carbon atoms, a cycloalkyl group having 3 to 20 carbon atoms, an aryl group having 6 to 20 carbon atoms, an alkylaryl group having 7 to 20 carbon atoms, or an arylalkyl group having 7 to 20 carbon atoms, which is substituted or unsubstituted, $R^4$, $R^5$, $R^6$, $R^7$, $R^8$, $R^9$, $R^{10}$, $R^{11}$ and $R^{12}$ each independently represent a hydrogen atom, a halogen atom, or a linear or branched alkyl group having 1 to 8 carbon atoms or a linear or branched alkenyl group having 2 to 8 carbon atoms, which is substituted or unsubstituted, and $R^{13}$ and $R^{14}$ each independently represent a hydrogen atom or a hydroxy group.

Here, a methylene group in a linear or branched alkyl group represented by $R^1$, $R^2$, $R^3$, and R, which has 1 to 20 carbon atoms and is substituted or unsubstituted, and in a linear or branched alkyl group represented by $R^4$, $R^5$, $R^6$, $R^7$, $R^8$, $R^9$, $R^{10}$, $R^{11}$, and $R^{12}$, which has 1 to 8 carbon atoms and is substituted or unsubstituted, may be substituted with at least one or more structures selected from an oxygen atom, a sulfur atom, a carbon-carbon double bond, —CO—, —CO—O—, —OC—O—, —CO—NH—, —NH—CO—, —$CR^{01}$=N—, and —N=$CR^{02}$, and $R^{01}$ and $R^{02}$ in the structures each independently represent a linear or branched alkyl group having 1 to 8 carbon atoms.

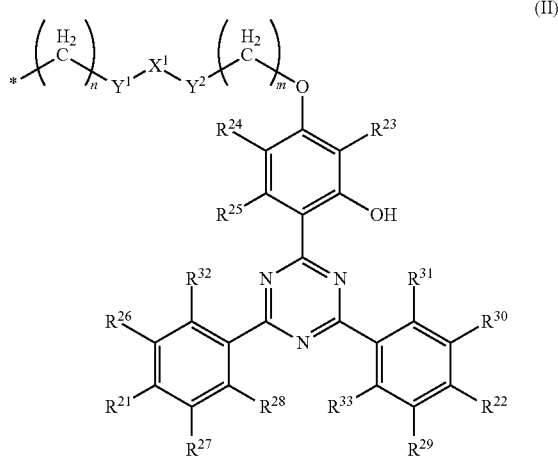

In General Formula (II), $R^{21}$ and $R^{22}$ each independently represent a hydrogen atom, a linear or branched alkyl group having 1 to 20 carbon atoms, which is substituted or unsubstituted, or —O—R, where R represents a linear or branched alkyl group having 1 to 20 carbon atoms, which is substituted or unsubstituted, a cycloalkyl group having 3 to 20 carbon atoms, an aryl group having 6 to 20 carbon atoms, an alkylaryl group having 7 to 20 carbon atoms, or an arylalkyl group having 7 to 20 carbon atoms, $R^{23}$, $R^{24}$, $R^{25}$, $R^{26}$, $R^{27}$, $R^{28}$, $R^{29}$, $R^{30}$, and Rn each independently represent a hydrogen atom, a halogen atom, or a linear or branched alkyl group having 1 to 8 carbon atoms or a linear or branched alkenyl group having 2 to 8 carbon atoms, which is substituted or unsubstituted, $R^{32}$ and $R^{33}$ each independently represent a hydrogen atom or a hydroxy group, $X^1$ represents a linear or branched alkylene group having 8 or more and 30 or fewer carbon atoms, which is substituted or unsubstituted, $Y^1$ and $Y^2$ each independently represent —CO—O—, —O—CO—, -$L^1$-, —O-$L^1$O—, —O-$L^1$-, -$L^1$-O—CO—, -$L^1$-CO—O—, —O—CH=CH—, —CH=CH—CO—, —CH=CH—CO—O—, —CH=CH—O—CO—, and —COO—CH=CH—, $L^1$ is a linear or branched alkylene group having 1 to 8 carbon atoms, m and n each independently represent an integer of 0 to 8, and * represents a bond with an oxygen atom linked to $R^1$ in Formula (I).

Here, a methylene group in a linear or branched alkyl group represented by $R^{21}$, $R^{22}$, and R, which has 1 to 20 carbon atoms and is substituted or unsubstituted, in a linear or branched alkyl group represented by $R^{23}$, $R^{24}$, $R^{25}$, $R^{26}$, $R^{27}$, $R^{28}$, $R^{29}$, $R^{30}$, and $R^{31}$, which has 1 to 8 carbon atoms and is substituted or unsubstituted, and in a linear or branched alkylene group represented by $X^1$, which has 8 to 30 carbon atoms, may be substituted with at least one or more structures selected from an oxygen atom, a sulfur atom, a carbon-carbon double bond, —CO—, —CO—O—, —OC—O—, —CO—NH—, —NH—CO—, —$CR^{03}$=N—, and —N=$CR^{04}$—, and $R^{03}$ and $R^{04}$ each independently represent a linear or branched alkyl group having 1 to 8 carbon atoms.

Examples of the linear or branched alkyl group having 1 to 20 carbon atoms represented by $R^1$, $R^2$, and $R^3$ in General Formula (I) and $R^{21}$, $R^{22}$, and R in General Formula (II), which is substituted or unsubstituted, include linear or branched alkyl groups such as methyl, ethyl, propyl, isopropyl, butyl, isobutyl, sec-butyl, tert-butyl, amyl, isoamyl, tert-amyl, hexyl, heptyl, n-octyl, isooctyl, tert-octyl, 2-ethylhexyl, nonyl, isononyl, decyl, undecyl, and dodecyl.

Examples of the cycloalkyl group having 3 to 20 carbon atoms, which is represented by $R^1$ and R in General Formula (I), include cyclopropyl, cyclopentyl, cyclohexyl, and cycloheptyl.

Examples of the aryl group having 6 to 20 carbon atoms, which is represented by $R^1$ and R in General Formula (I) include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, 2,5-di-tert-butylphenyl, 2,6-di-tert-butylphenyl, 2,4-di-tert-pentylphenyl, 2,5-di-tert-amylphenyl, 2,5-di-tert-octylphenyl, biphenyl, and, 2,4,5-trimethylphenyl.

Examples of the arylalkyl group having 7 to 20 carbon atoms, which is represented by $R^1$ and R in General Formula (I) include benzyl, phenethyl, 2-phenylpropan-2-yl, and diphenylmethyl.

Examples of the alkylaryl group having 7 to 20 carbon atoms, which is represented by $R^1$ and R in General Formula (I) include a group in which one hydrogen atom of the above alkyl group is substituted with an aryl group. Examples of the aryl group include phenyl, cresyl, xylyl, 2,6-xylyl, 2,4,6-trimethylphenyl, butylphenyl, nonylphenyl, biphenyl, naphthyl, and anthracenyl.

Examples of the halogen atom represented by $R^4$, $R^5$, $R^6$, $R^7$, $R^8$, $R^9$, $R^{10}$, $R^{11}$, and $R^{12}$ in General Formula (I) and $R^{23}$, $R^{24}$, $R^{25}$, $R^{26}$, $R^{27}$, $R^{28}$, $R^{29}$, $R^{30}$, and $R^{31}$ in General Formula (II) and include fluorine, chlorine, bromine, and iodine.

Examples of the linear or branched alkyl group having 1 to 8 carbon atoms, which is represented by $R^4$, $R^5$, $R^6$, $R^7$, $R^8$, $R^9$, $R^{10}$, $R^{11}$, and $R^{12}$ in General Formula (I) and $R^{23}$, $R^{24}$, $R^{25}$, $R^{26}$, $R^{27}$, $R^{28}$, $R^{29}$, $R^{30}$, and $R^{31}$ in General Formula (II) and is substituted or unsubstituted, include methyl, ethyl, propyl, isopropyl, butyl, isobutyl, sec-butyl, tert-butyl, amyl, isoamyl, tert-amyl, hexyl, heptyl, n-octyl, isooctyl, tert-octyl, and 2-ethylhexyl. In the particulate ultraviolet absorber of the present embodiment, an alkyl group having 1 to 8 carbon atoms is preferable.

Examples of the linear or branched alkenyl group having 2 to 8 carbon atoms, which is represented by $R^1$, $R^4$, $R^5$, $R^6$, $R^7$, $R^8$, $R^9$, $R^{10}$, $R^{11}$, and $R^{12}$ in General Formula (I) and $R^{23}$, $R^{24}$, $R^{25}$, $R^{26}$, $R^{27}$, $R^{28}$, $R^{29}$, $R^{30}$, and $R^{31}$ in General Formula (II), include linear and branched propenyl, butenyl, pentenyl, hexenyl, heptenyl, and octenyl irrespective of the position of an unsaturated bond.

The linear or branched alkylene group having 8 or more and 30 or fewer carbon atoms, which is represented by X1 in General Formula (II) and is substituted or unsubstituted, represents an alkylene group in which 8 or more and 30 or less of methylene are linked or an alkylene group in which a part of hydrogen atoms of methylene are substituted with alkyl groups. In the particulate ultraviolet absorber of the present embodiment, an alkylene group having carbon atoms of 8 or more and 20 or less is preferable.

In General Formula (II), examples of the linear or branched alkylene group having 1 to 8 carbon atoms represented by $L^1$ include methylene, methylmethylene, dimethylmethylene, ethylene, propylene, isopropylene, butylene, isobutylene, and pentylene.

The triazine-based compound may contain compounds in which $R^5$, $R^6$, $R^8$, $R^9$, $R^{11}$, and $R^{12}$ in General Formula (I) are hydrogen atoms.

In addition, examples of the triazine-based compound represented by General Formula (I) include compounds represented by General Formula (A) or compounds represented by General Formula (B).

In addition, as the particulate ultraviolet absorber of the present embodiment, a compound represented by General Formula (A) can be used. These compounds may be used alone or in the combination of two or more thereof.

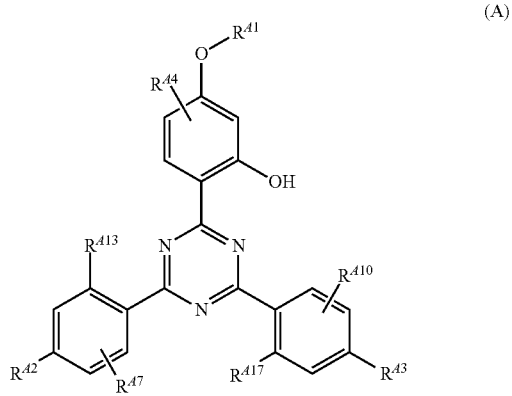

In General Formula (A), $R^{A1}$ represents a linear or branched alkyl group having 1 to 12 carbon atoms, a cycloalkyl group having 3 to 8 carbon atoms, a linear or branched alkenyl group having 3 to 8 carbon atoms, an aryl group having 6 to 18 carbon atoms, an alkylaryl group having 7 to 18 carbon atoms, or an arylalkyl group having 7 to 18 carbon atoms, $R^{A2}$ and $R^{A3}$ may be the same or different from each other and represent a hydrogen atom, a linear or branched alkyl group having 1 to 12 carbon atoms, or a linear or branched alkoxy group having 1 to 12 carbon atoms, $R^{A4}$, $R^{A7}$, and $R^{A10}$ may be the same or different from each other and represent a hydrogen atom, a linear or branched alkyl group having 1 to 8 carbon atoms, or a linear or branched alkenyl group having 3 to 8 carbon atoms, and $R^{A13}$ and $R^{A17}$ may be the same or different from each other and represent a hydrogen atom or a hydroxy group.

Here, a methylene group in a linear or branched alkyl group represented by $R^{A1}$, $R^{A2}$, and $R^{A3}$, which has 1 to 12 carbon atoms, and in a linear or branched alkoxy group represented by $R^{A2}$ and $R^{A3}$, which has 1 to 12 carbon atoms, may be substituted with at least one or more structures selected from an oxygen atom, a sulfur atom, a carbon-carbon double bond, —CO—, —CO—O—, —OC—O—, —CO—NH—, —NH—CO—, —CR$^{O5}$=N—, and —N=CR$^{O6}$—, and $R^{O5}$ and $R^{O6}$ in the structures each independently represent a linear or branched alkyl group having 1 to 8 carbon atoms.

Examples of the linear or branched alkyl group having 1 to 12 carbon atoms, which is represented by $R^{A1}$, $R^{A2}$, and $R^{A3}$ in General Formula (A) include linear or branched alkyl group such as methyl, ethyl, propyl, isopropyl, butyl, isobutyl, sec-butyl, tert-butyl, amyl, isoamyl, tert-amyl, hexyl, heptyl, n-octyl, isooctyl, tert-octyl, 2-ethylhexyl, nonyl, isononyl, decyl, undecyl, and dodecyl.

Examples of the linear or branched alkoxy group having 1 to 12 carbon atoms, which is represented by $R^{A2}$ and $R^{A3}$ in General Formula (A) include, methyloxy, ethyloxy, isopropyloxy, butyloxy, sec-butyloxy, tert-butyloxy, isobutyloxy, amyloxy, isoamyloxy, tert-amyloxy, hexyloxy, 2-hexyloxy, 3-hexyloxy, cyclohexyloxy, 4-methylcyclohexyloxy, heptyloxy, 2-heptyloxy, 3-heptyloxy, isoheptyloxy, tert-heptyloxy, 1-octyloxy, isooctyloxy, and tert-octyloxy.

Examples of the cycloalkyl group having 3 to 8 carbon atoms, which is represented by $R^{A1}$ in General Formula (A), include cyclopropyl, cyclopentyl, cyclohexyl, and cycloheptyl.

Examples of the aryl group having 6 to 18 carbon atoms or the alkylaryl group having 7 to 18 carbon atoms, which is represented by $R^{A1}$ in General Formula (A), include phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, 2,5-di-tert-butylphenyl, 2,6-di-tert-butylphenyl, 2,4-di-tert-pentylphenyl, 2,5-di-tert-amylphenyl, 2,5-di-tert-octylphenyl, biphenyl, and 2,4,5-trimethylphenyl. Examples of the arylalkyl group having 7 to 18 carbon atoms include benzyl, phenethyl, 2-phenylpropan-2-yl, and diphenylmethyl.

Examples of the linear or branched alkenyl group having 3 to 8 carbon atoms, which is represented by $R^{A1}$, $R^{A4}$, $R^{A7}$, and $R^{A10}$ in General Formula (A), include linear and branched propenyl, butenyl, pentenyl, hexenyl, heptenyl, and octenyl irrespective of the position of an unsaturated bond.

Examples of the linear or branched alkyl group having 1 to 8 carbon atoms, which is represented by $R^{A4}$, $R^{A7}$, and $R^{A10}$ in General Formula (A) include methyl, ethyl, propyl, isopropyl, butyl, sec-butyl, tert-butyl, isobutyl, amyl, tert-amyl, octyl, and tert-octyl. Among these, a methyl group is preferable since it has an excellent ultraviolet absorption ability.

The triazine-based compound represented by General Formula (A) is preferably one or two or more triazine-based compounds represented by any of Compound No. 1A to Compound No. 5A.

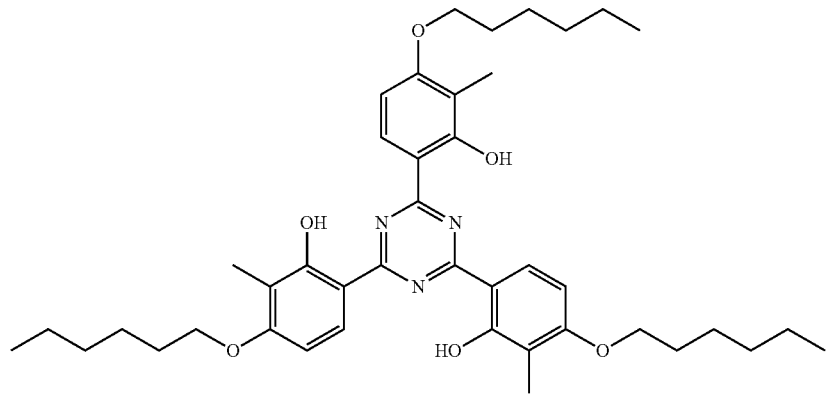
Compound No. 1A
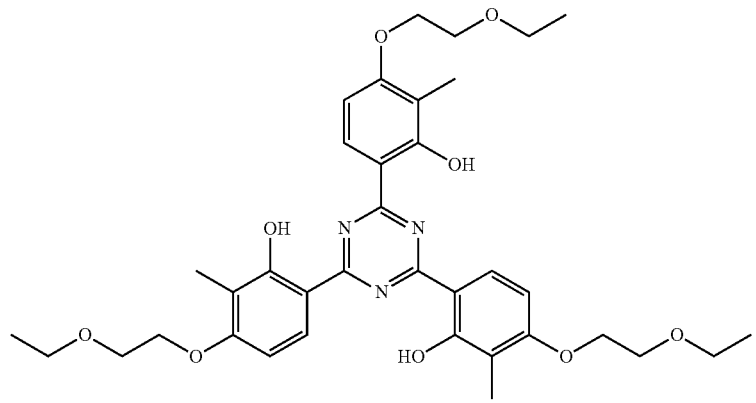
Compound No. 2A
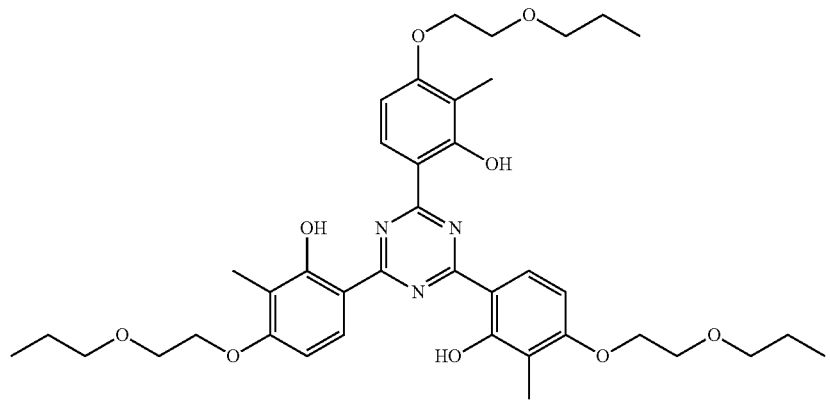
Compound No. 3A
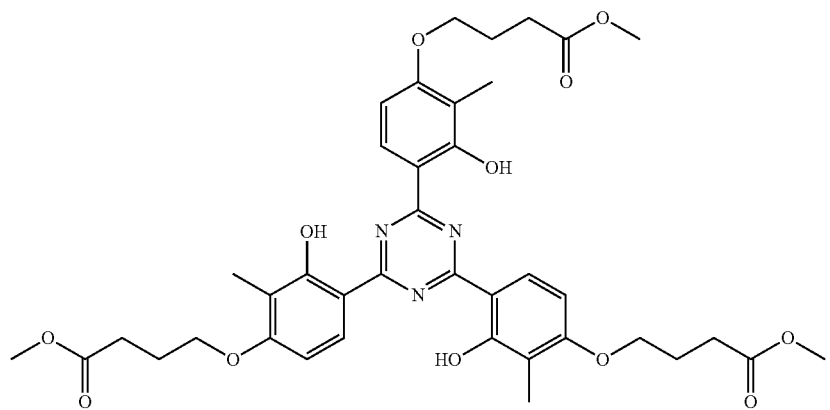
Compound No. 4A -continued Compound No. 5A

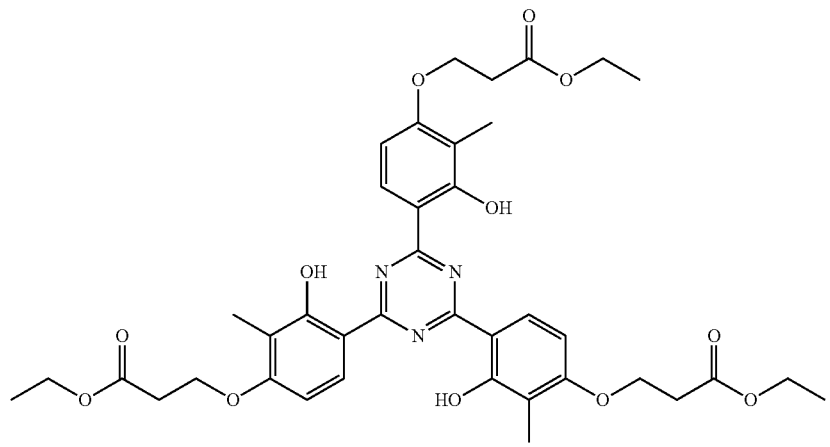

In addition, the triazine-based compound represented by General Formula (A) is preferably one or two or more triazine-based compounds represented by any of Compound No. 6A to Compound No. 8A.

Compound No. 6A

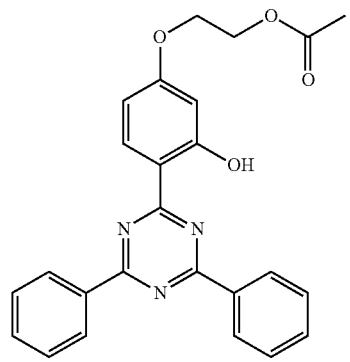

Compound No. 7A

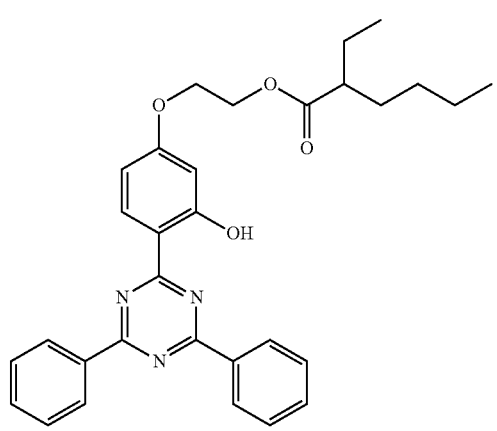

-continued

Compound No. 8A

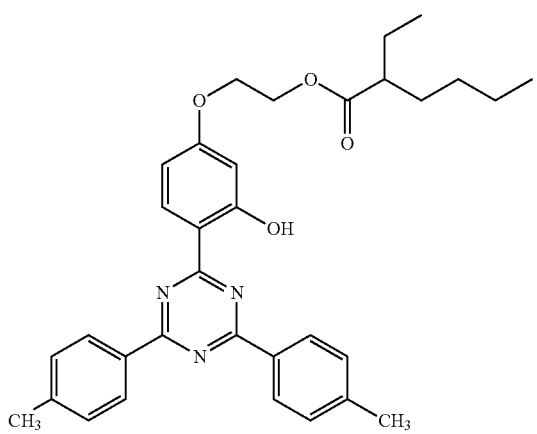

In addition, as the particulate ultraviolet absorber of the present embodiment, a compound represented by General Formula (B) can be used. These compounds may be used alone or in the combination of two or more thereof.

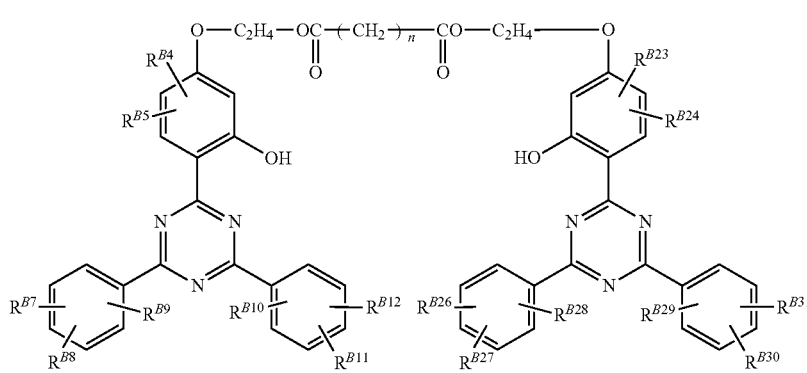

(B)

In General Formula (B), $R^{B4}$, $R^{B5}$, $R^{B7}$ to $R^{B9}$, $R^{B10}$ to $R^{B12}$, $R^{B23}$, $R^{B24}$, $R^{B26}$ to $R^{B28}$, and $R^{B29}$ to $R^{B31}$ each independently represent a hydrogen atom, a hydroxy group, a halogen atom, a linear or branched alkyl group having 1 to 8 carbon atoms, a linear or branched alkenyl group having 2 to 8 carbon atoms, a linear or branched alkoxy group having 1 to 20 carbon atoms, or an aryl group having 6 to 20 carbon atoms, and n represents an integer of 8 to 14. Here, a para-position of two of three benzene rings linked to a triazine ring represents a hydrogen atom, a linear or branched alkyl group having 1 to 20 carbon atoms, or a linear or branched alkoxy group having 1 to 20 carbon atoms, and one of ortho-positions represents a hydrogen atom or a hydroxy group.

Examples of the halogen atom represented by $R^{B4}$, $R^{B5}$, $R^{B7}$ to $R^{B9}$, $R^{B10}$ to $R^{B12}$, $R^{B23}$, $R^{B24}$, $R^{B26}$ to $R^{B28}$, and $R^{B29}$ to $R^{B31}$ in General Formula (B) include a fluorine atom, a chlorine atom, and a bromine atom.

Examples of the linear or branched alkyl group having 1 to 20 carbon atoms, which is represented by $R^{B4}$, $R^{B5}$, $R^{B7}$ to $R^{B9}$, $R^{B10}$ to $R^{B12}$, $R^{B23}$, $R^{B24}$, $R^{B26}$ to $R^{B28}$, and $R^{B29}$ to $R^{B31}$ in General Formula (B) include methyl, ethyl, propyl, 2-propynyl, butyl, isobutyl, sec-butyl, tert-butyl, pentyl, isopentyl, hexyl, decyl, dodecyl, and octadecyl.

Examples of the linear or branched alkenyl group having 2 to 8 carbon atoms, which is represented by $R^{B4}$, $R^{B5}$, $R^{B7}$ to $R^{B9}$, $R^{B10}$ to $R^{B12}$, $R^{B23}$, $R^{B24}$, $R^{B26}$ to $R^{B28}$, and $R^{B29}$ to $R^{B31}$ in General Formula (B) include vinyl, 1-propenyl, isopropenyl, 2-methyl-1-propenyl, 1-butenyl, 2-butenyl, 3-butenyl, 2-ethyl-1-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, and 5-hexenyl.

Examples of the linear or branched alkoxy group having 1 to 20 carbon atoms, which is represented by $R^{B4}$, $R^{B5}$, $R^{B7}$ to $R^{B9}$, $R^{B10}$ to $R^{B12}$, $R^{B23}$, $R^{B24}$, $R^{B26}$ to $R^{B28}$, and $R^{B29}$ to $R^{B31}$ in General Formula (B) include, methyloxy, ethyloxy, isopropyloxy, butyloxy, sec-butyloxy, tert-butyloxy, isobutyloxy, amyloxy, isoamyloxy, tert-amyloxy, hexyloxy, 2-hexyloxy, 3-hexyloxy, cyclohexyloxy, 4-methylcyclohexyloxy, heptyloxy, 2-heptyloxy, 3-heptyloxy, isoheptyloxy, tert-heptyloxy, 1-octyloxy, isooctyloxy, and tert-octyloxy.

Examples of the aryl group having 6 to 20 carbon atoms, which is represented by $R^{B4}$, $R^{B5}$, $R^{B7}$ to $R^{B9}$, $R^{B10}$ to $R^{B12}$, $R^{B23}$, $R^{B24}$, $R^{B26}$ to $R^{B28}$, and $R^{B29}$ to $R^{B31}$ in General Formula (B) include phenyl, naphthyl, anthracenyl, phenanthryl, fluorenyl, indenyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl)phenyl, 4-stearylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, 2,5-di-tert-butylphenyl, 2,6-di-tert-butylphenyl, 2,4-di-tert-pentylphenyl, 2,5-di-tert-amylphenyl, 2,5-di-tert-octylphenyl, 2,4-dicumylphenyl, 4-cyclohexylphenyl, (1,1'-biphenyl)-4-yl, 2,4,5-trimethylphenyl, and ferrocenyl.

In addition, the triazine-based compound represented by General Formula (B) is preferably one or two or more triazine-based compounds represented by any of Compound No. 1B to Compound No. 4B.

Compound No. 1B

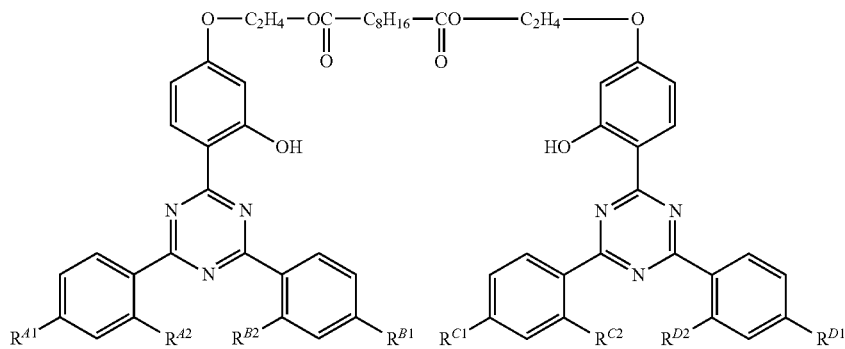

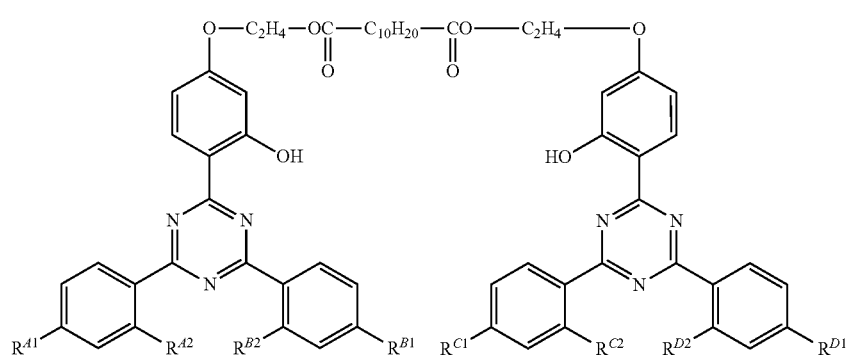

Compound No. 2B

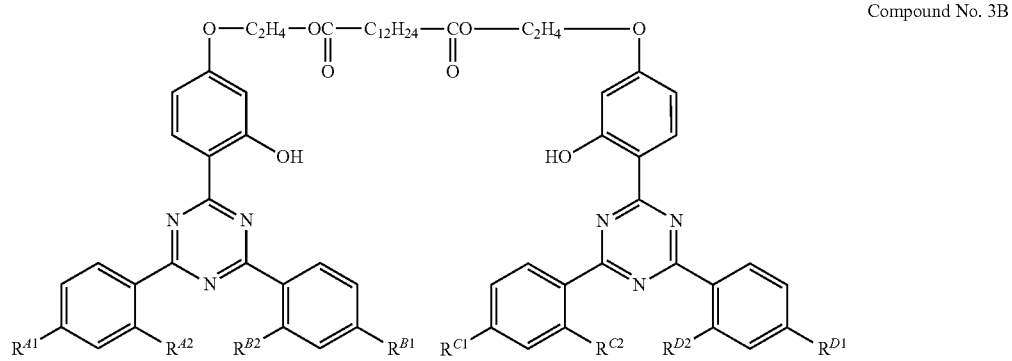

Compound No. 3B

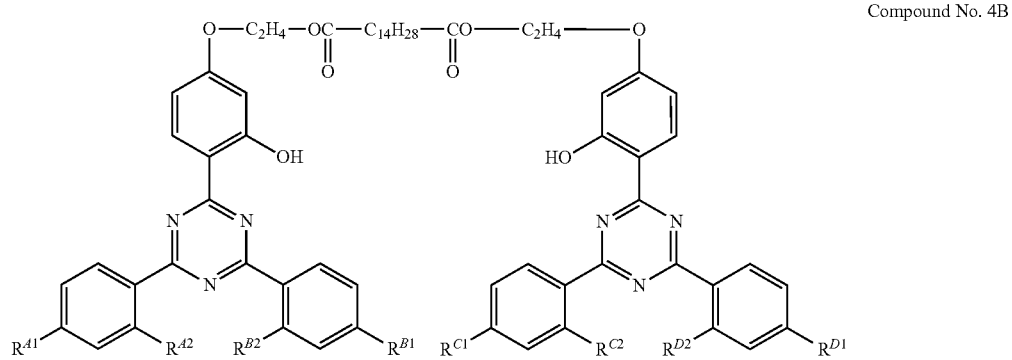

Compound No. 4B

In Compound No. 1B to Compound No. 4B, $R^{A1}$, $R^{A2}$, $R^{B1}$, $R^{B2}$, $R^{C1}$, $R^{C2}$, $R^{D1}$, and $R^{D2}$ may be the same or different from each other and represent a hydrogen atom, a linear or branched alkyl group having 1 to 4 carbon atoms, or a linear or branched alkoxy group having 1 to 4 carbon atoms.

The method for synthesizing the triazine-based compound is not particularly limited and may be any of the synthesizing methods usually used for synthesizing a compound having a triazine structure. Examples of the synthesizing method include a method of performing an addition reaction in which a phenol derivative or a resorcinol derivative is added to cyanuric chloride using aluminum trichloride. The substituent provided on the benzene ring linked to the triazine ring by a single bond may be introduced after forming the triazine structure or may be introduced into the phenol compound or the resorcinol derivative before forming the triazine structure.

Examples of the method for synthesizing the triazine-based compound include an esterification reaction or transesterification reaction with a corresponding ester-inducible compound (a carboxylic acid, a carboxylic acid halide, a carboxylic acid ester), using 2-[2-hydroxy-4-(2-hydroxyethyloxy)phenyl]-4,6-diphenyl-1,3,5-tri azine as an alcohol component, and these reactions may be a sequential reaction or a batch reaction.

Examples of the alcohol component include an ester-inducible compound (a monovalent carboxylic acid, a monovalent carboxylic acid halide, or a monovalent carboxylic acid ester) of a monovalent carboxylic acid and an ester-inducible compound (a divalent carboxylic acid, a divalent carboxylic acid halide, or a divalent carboxylic acid ester) of a divalent carboxylic acid.

The triazine-based compound may be purified after synthesis. As the purification method, distillation, recrystallization, reprecipitation, a method using a filtering agent and an adsorbent, or the like can be appropriately used. These compounds may be used alone or in the combination of two or more thereof.

As necessary, the triazine-based compound can be subjected to processing such as pulverization, granulation, classification, and melting solidification after purification. These compounds may be used alone or in the combination of two or more thereof. As a result, the desired powder characteristics of the particulate triazine-based compound can be obtained.

The particle shape of the particulate ultraviolet absorber of the present embodiment means a powder form or a granule form. This particulate ultraviolet absorber may be directly used in the powder form or granule form but may be used after being processed into a certain shape such as pellets, briquettes, and tablets.

The particulate ultraviolet absorber of the present embodiment has the characteristics defined by the compressibility described below.

In the present embodiment, the compressibility is measured under the following measurement condition.

First, a predetermined container is filled with the particulate ultraviolet absorber, the particulate ultraviolet absorber is leveled off without tapping, and then the loose bulk density (g/cm$^3$) of the particulate ultraviolet absorber in the container is measured.

Subsequently, a predetermined container is filled with the particulate ultraviolet absorber, the particulate ultraviolet absorber is tapped from a height of 18 mm under a condition of 180 times of tapping and, leveled off, and then the tight bulk density (g/cm$^3$) of the particulate ultraviolet absorber in the container is measured.

In a case where the loose bulk density is denoted by D1 and the tight bulk density is denoted by D2, the compressibility (%) is calculated based on expression: [(D2−D1)/D2]×100.

The lower limit of the compressibility of the particulate ultraviolet absorber of the present embodiment is 5.0% or more, preferably 5.5% or more, and more preferably 6.0% or more. Thereby, the compression granulation property can be improved. On the other hand, the upper limit of the compressibility of the particulate ultraviolet absorber is 40% or less, preferably 35% or less, more preferably 30% or less, and still more preferably 25% or less. Thereby, the feeding property can be improved.

The loose bulk density of the particulate ultraviolet absorber is, for example, 0.20 g/cm$^3$ to 0.70 g/cm$^3$, preferably 0.30 to 0.65, and more preferably 0.42 to 0.60. By setting the numerical values within the above ranges, it is possible to realize a particulate ultraviolet absorber excellent the powder characteristics and the ultraviolet absorbing characteristics.

In addition, the tight bulk density of the particulate ultraviolet absorber is, for example, 0.40 g/cm$^3$ to 0.90 g/cm$^3$, preferably 0.45 to 0.80, and more preferably 0.50 to 0.70. By setting the numerical values within the above ranges, it is possible to realize a particulate ultraviolet absorber excellent the powder characteristics and the ultraviolet absorbing characteristics.

In the present embodiment, it is possible to control the compressibility, the loose bulk density, and the tight bulk density by appropriately selecting the type and form of the triazine-based compound, the method for preparing the triazine-based compound, and the like. Among these, for example, appropriately adopting the processing conditions of the triazine-based compound, such as melting solidification and pulverization and classification, is a factor to set the compressibility, the loose bulk density, and the tight bulk density within the desired numerical range.

In addition, as a result of further study, the inventors of the present invention have found that the powder characteristics of a triazine-based compound or a particulate ultraviolet absorber using the triazine-based compound can be appropriately controlled by using an X-ray diffraction analysis pattern as an index. Further intensive studies based on such findings have revealed that by setting the diffraction angle 2θ having the maximum peak in the powder X-ray diffraction analysis pattern within a predetermined numerical range, it is possible to improve the powder characteristics of the above triazine-based compound and the particulate ultraviolet absorber using the triazine-based compound.

The triazine-based compound (the particulate ultraviolet absorber) of the present embodiment may have the characteristics defined by the following powder X-ray diffraction analysis pattern.

In the triazine-based compound of the present embodiment, a maximum peak in a powder X-ray diffraction analysis pattern may be within a range in which a diffraction angle 2θ is 5.00° or more and 6.50° or less, preferably 5.20° or more and 6.00° or less, and more preferably 5.40° or more and 5.80° or less. As a result, since the feeding property and the compression granulation property can be enhanced, a triazine-based compound and a particulate ultraviolet absorber having excellent powder characteristics can be realized.

Here, the maximum peak has the maximum peak intensity in the X-ray diffraction pattern obtained within the scanning range (for example, diffraction angle 2θ=3° to 60° or 3° to 90°) in the powder X-ray diffraction measurement.

In addition, in the powder X-ray diffraction analysis pattern of the triazine-based compound, a half-width of the maximum peak is, for example, 0.05° or more and 0.20° or less, preferably 0.10° or more and 0.19° or less, and more preferably 0.15° or more and 0.18° or less. By appropriately setting to the peak width of the maximum peak so that the numerical range is within the above ranges, it is possible to realize a particulate ultraviolet absorber excellent the powder characteristics and the ultraviolet absorbing characteristics.

In addition, in the powder X-ray diffraction analysis pattern of the triazine-based compound, in a case where the relative intensity of the maximum peak is set to 100, the diffraction angle 2θ range is configured such that, for example, a diffraction peak having a relative intensity of 30 or more and 60 or less, preferably having a relative intensity of 25 or more and 60 or less, and more preferably having a relative intensity of 22 or more and 60 or less is not present within a range in which a diffraction angle 2θ is 3.0° or more and 45.0° or less. That is, by setting the peak intensity of the maximum peak value relatively high, it is possible to realize a particulate ultraviolet absorber excellent the powder characteristics and the ultraviolet absorbing characteristics.

In addition, in the powder X-ray diffraction analysis pattern of the triazine-based compound, in a case where the relative intensity of the maximum peak is set to 100, the diffraction angle 2θ range is configured such that, for example, a diffraction peak having a relative intensity of 1 or more and 5 or less is not present within a range in which a diffraction angle 2θ is more than 45.0° and 60.0° or less and preferably more than 45.0° and 90.0° or less. That is, by setting a region in which a peak having weak intensity is not present within the appropriate numerical range, it is possible to realize a particulate ultraviolet absorber excellent the powder characteristics and the ultraviolet absorbing characteristics.

In the present embodiment, it is possible to control the powder X-ray diffraction analysis pattern including such as the diffraction angle 2θ of the maximum peak and the half-width of the maximum peak by appropriately selecting the type and form of the triazine-based compound, the method for preparing the triazine-based compound, and the like. Among these, for example, appropriately adopting the processing conditions of the triazine-based compound, such as melting solidification and pulverization and classification, is a factor to set the powder X-ray diffraction analysis pattern including such as the diffraction angle 2θ of the maximum peak and the half-width of the maximum peak within the desired numerical range.

A resin composition of the present embodiment will be described.

The resin composition contains the particulate ultraviolet absorber described above. This resin composition may contain a synthetic resin. Thereby, desired resin characteristics according to various uses can be obtained.

Examples of the synthetic resin include a thermoplastic resin, a thermosetting resin, and an elastomer. These compounds may be used alone or in the combination of two or more thereof.

Specific examples of the synthetic resin include the followings.

Examples of the thermoplastic resin include; α-Olefin polymers or ethylene-vinyl acetate copolymers such as polypropylene, a high density polyethylene, a low density polyethylene, a linear low density polyethylene, a cross-linked polyethylene, an ultra high molecular weight polyethylene, polybutene-1, and poly-3-methylpentene, polyolefins and copolymers thereof such as an ethylene-ethyl acrylate copolymer and an ethylene-propylene copolymer, and halogen-containing resins such as polyvinyl chloride, polyvinylidene chloride, chlorinated polyethylene, chlorinated polypropylene, polyvinylidene fluoride, chlorinated rubber, a vinyl chloride-vinyl acetate copolymer, a vinyl chloride-ethylene copolymer, a vinyl chloride-vinylidene chloride copolymer, a vinyl chloride-vinylidene chloride-vinyl acetate terpolymer, a vinyl chloride-acrylic acid ester copolymer, a vinyl chloride-maleic acid ester copolymer, and a vinyl chloride-cyclohexylmaleimide copolymer; a petroleum resin, a coumarone resin, polystyrene, polyvinyl acetate, an acrylic resin, polymethylmethacrylate, polyvinyl alcohol, polyvinyl formal, and polyvinyl butyral; polyalkylene terephthalates such as polyethylene terephthalate, polybutylene terephthalate, and poly cyclohexane dimethylene terephthalate, aromatic polyesters such as polyalkylene naphthalate such as polyethylene naphthalate and polybutylene naphthalate, and a linear polyester such as polytetramethylene terephthalate; degradable aliphatic polyester such as polyhydroxybutyrate, polycaprolactone, polybutylene succinate, polyethylene succinate, a polylactic acid resin, polymalic acid, polyglycolic acid, polydioxane, and poly(2-oxetanone); and polyamides such as polyphenylene oxide, polycaprolactam, and polyhexamethylene adipamide, polycarbonate, a branched polycarbonate, polyacetal, polyphenylene sulfide, polyurethane, and a fiber-based resin.

Examples of the thermosetting resin include a phenol resin, a urea resin, a melamine resin, an epoxy resin, and an unsaturated polyester resin.

In addition, examples of the elastomer include a fluororesin, a silicone resin, a silicone rubber polyethersulfone, polysulfone, polyphenylene ether, polyetherketone, polyetheretherketone, and a liquid crystal polymer. Further, examples of the elastomer include isoprene rubber, butadiene rubber, acrylonitrile-butadiene copolymer rubber, styrene-butadiene copolymer rubber, fluororubber, and silicone rubber.

More specific examples of the elastomers include an olefin-based thermoplastic elastomer, a styrene-based thermoplastic elastomer, a polyester-based thermoplastic elastomer, a nitrile-based thermoplastic elastomer, a nylon-based thermoplastic elastomer, a vinyl chloride-based thermoplastic elastomer, and a polyamide-based thermoplastic elastomer, and a polyurethane-based thermoplastic elastomer.

Further, examples of the synthetic resin having excellent transparency include copolymers of polyethylene, polypropylene, polystyrene, and polyethylene with cycloolefin such as norbornene, vinyl compounds such as polyacrylic acid, polyacrylic acid ester, polyvinyl acetate, polyacrylonitrile, polyvinyl chloride, and polyvinyl fluoride and addition polymers of vinyl compounds, vinyl compound such as polymethacrylic acid, polymethacrylic acid ester, polyvinylidene chloride, polyvinylidene fluoride, polyvinylidene cyanide, a vinylidene fluoride/trifluoroethylene copolymer, a vinylidene fluoride/tetrafluoroethylene copolymer, a copolymer of a vinylidene cyanide/vinyl acetate or a copolymer of a fluorine-based compound, compounds containing fluorine such as polytrifluoroethylene, polytetrafluoroethylene, and polyhexafluoropropylene, polyamides such as nylon 6 and nylon 66, polyimide, polyurethane, polypeptide, polybutylene terephthalate, polyester such as polyethylene terephthalate, polyethers such as polycarbonate, polyoxymethylene, polyethylene oxide, and polypropylene oxide, an epoxy resin, polyvinyl alcohol, and polyvinyl butyral.

From the viewpoint of compatibility and transparency, examples of the synthetic resin include a polycarbonate resin, a polyester resin, an acrylic resin, and an ABS resin.

The above-described synthetic resins may be used alone or in the combination of two or more thereof and may be alloyed.

The blending amount of the particulate ultraviolet absorber in the resin composition is, for example, preferably 0.001 to 20 parts by mass, more preferably 0.01 to 10 parts by mass, and still more preferably 0.1 to 5 parts by mass with respect to 100 parts by mass of a synthetic resin. In a case where the blending amount is equal to or more than the lower limit, a sufficient effect of the particulate ultraviolet absorber can be obtained. Further, in a case where the blending amount is equal to or less than the upper limit, desired physical properties of a resin can be obtained while achieving the improved effect of adding a particulate ultraviolet absorber.

In the present specification, "to" means that an upper limit and a lower limit are included unless otherwise specified.

The resin composition of the present embodiment can include other additive components other than the components described above, as necessary. Examples of other additive components include an antioxidant, an ultraviolet absorber other than the triazine-based compound according to the present embodiment, a hindered amine-based light stabilizer, a near-infrared absorber, a nucleating agent (transparentizing agent), an antistatic agent, a lubricant, a plasticizer, a light absorbing dye, a filling agent (filler), pigment, dyestuff, metal soap, a processing aid, a flame retardant, a flame retardant aid, a zeolite compound, a foaming agent, a (heavy) metal deactivator, a cross-linking agent, an epoxy stabilizer, a matte agent, an anti-fogging agent, a plate-out preventing agent, a surface treatment agent, a fluorescent whitening agent, an antifungal agent, an antibacterial agent, and a releasing agent.

Examples of the antioxidant include a phenol-based antioxidant, a phosphorus-based antioxidant, and a sulfur-based antioxidant.

Examples of the phenolic antioxidant include 2,6-di-tert-butyl-p-cresol, 2,6-diphenyl-4-octadecyloxyphenol, distearyl(3,5-di-tert-butyl-4-hydroxybenzyl)phosphonate, 1,6-hexamethylenebis[(3,5-di-tert-butyl-4-hydroxyphenyl)

propionic acid amide], 4,4'-thiobis(6-tert-butyl-m-cresol), 2,2'-methylenebis(4-methyl-6-tert-butylphenol), 2,2'-methylenebis(4-ethyl-6-tert-butylphenol), 4,4'-butylidenebis(6-tert-butyl-m-cresol), 2,2'-ethylidenebis(4,6-di-tert-butylphenol), 2,2'-ethylidenebis(4-sec-butyl-6-tert-butylphenol), 1,1,3-tris(2-methyl-4-hydroxy-5-tert-butylphenyl)butane, 1,3,5-tris(2,6-dimethyl-3-hydroxy-4-tert-butylbenzyl) isocyanurate, 1,3,5-tris(3,5-di-tert-butyl-4-hydroxybenzyl) isocyanurate, 1,3,5-tris(3,5-di-tert-butyl-4-hydroxybenzyl)-2,4,6-trimethylbenzene, 2-tert-butyl-4-methyl-6-(2-acryloyloxy-3-tert-butyl-5-methylbenz yl) phenol, stearyl(3,5-di-tert-butyl-4-hydroxyphenyl)propionate, tetrakis[3-(3,5-di-tert-butyl-4-hydroxyphenyl)methyl propionate]methane, thiodiethylene glycol bis[(3,5-di-tert-butyl-4-hydroxyphenyl)propionate], 1,6-hexamethylenebis[(3,5-di-tert-butyl-4-hydroxyphenyl)propionate], bis[3,3-bis(4-hydroxy-3-tert-butylphenyl)butyric acid]glycol ester, bis[2-tert-butyl-4-methyl-6-(2-hydroxy-3-tert-butyl-5-methylbenz yl)phenyl] terephthalate, 1,3,5-tris[(3,5-di-tert-butyl-4-hydroxyphenyl)propionyloxyethyl]isocyanurate, 3,9-bis[1,1-dimethyl-2-{(3-tert-butyl-4-hydroxy-5-methylphenyl) propionyloxy}ethyl]-2,4,8,10-tetraoxaspiro[5,5]undecane, triethylene glycol bis[(3-tert-butyl-4-hydroxy-5-methylphenyl)propionate].

Examples of the phosphorus-based antioxidant include trisnonylphenyl phosphite, tris[2-tert-butyl-4-(3-tert-butyl-4-hydroxy-5-methylphenylthio)-5-methylphenyl]phosphite, tridecyl phosphite, triisodecyl phosphite, trilauryl phosphite, octyl diphenyl phosphite, di(decyl)monophenyl phosphite, di(tridecyl)pentaerythritol diphosphite, di(nonylphenyl)pentaerythritol diphosphite, bis(2,4-di-tert-butylphenyl)pentaerythritol diphosphite, bis(2,6-di-tert-butyl-4-methylphenyl)pentaerythritol diphosphite, bis(2,4,6-tri-tert-butylphenyl)pentaerythritol diphosphite, bis(2,4-dicumylphenyl)pentaerythritol diphosphite, tetra(tridecyl) isopropylidene diphenol diphosphite, tetra(tridecyl)-4,4'-n-butylidene bis(2-tert-butyl-5-methylphenol)diphosphite, hexa(tridecyl)-1,1,3-tris(2-methyl-4-hydroxy-5-tert-butylphenyl) butane triphosphite, tetrakis(2,4-di-tert-butylphenyl)biphenylene diphosphonite, 9,10-dihydro-9-oxa-10-phosphaphenanthrene-10-oxide, 2,2'-methylene bis(4,6-tert-butylphenyl)-2-ethylhexylphosphite, 2,2'-methylene bis(4,6-tert-butylphenyl)-octadecyl phosphite, 2,2'-ethylidene bis(4,6-di-tert-butylphenyl)fluorophosphite, tris(2-[(2,4,8,10-tetrakis-tert-butyldibenzo[d,f][1,3,2]dioxaphosphepin-6-yl)oxy]ethyl) amine, and a phosphite of 2-ethyl-2-butylpropylene glycol and 2,4,6-tri-tert-butylphenol.

Examples of the sulfur-based antioxidant include dialkyl thiodipropionates such as dilauryl thiodipropionate, dimyristyl thiodipropionate, and distearyl thiodipropionate, and pentaerythritol tetra (β-alkylthiopropionate) esters.

Examples of the ultraviolet absorber other than the triazine-based compound according to the present embodiment include: 2-hydroxybenzophenones such as 2,4-dihydroxybenzophenone, 2-hydroxy-4-methoxybenzophenone, 2-hydroxy-4-octoxybenzophenone, and 5,5'-methylenebis(2-hydroxy-4-methoxybenzophenone); 2-(2'-hydroxyphenyl) benzotriazoles such as 2-(2'-hydroxy-5'-methylphenyl) benzotriazole such as 2-(2'-hydroxy-3',5'-di-tert-butylphenyl)-5-chlorobenzotriazole, 2-(2'-hydroxy-3'-tert-butyl-5'-methylphenyl)-5-chlorobenzotriazole, 2-(2'-hydroxy-5'-tert-octylphenyl)benzotriazole, 2-(2'-hydroxy-3',5'-dicumylphenyl)benzotriazole, 2,2'-methylenebis(4-tert-octyl-6-(benzotriazolyl)phenol), and 2-(2'-hydroxy-3'-tert-butyl-5'-carboxyphenyl)benzotriazole; benzoates such as phenyl salicylate, resorcinol monobenzoate, 2,4-di-tert-butylphenyl-3,5-di-tert-butyl-4-hydroxybenzoate, 2,4-di-tert-amylphenyl-3,5-di-tert-butyl-4-hydroxybenzoate, and hexadecyl-3,5-di-tert-butyl-4-hydroxybenzoate; substituted oxanilides such as 2-ethyl-2'-ethoxyoxanilide and 2-ethoxy-4'-dodecyloxanilide; and cyanoacrylates such as ethyl-α-cyano-β,β-diphenylacrylate and methyl-2-cyano-3-methyl-3-(p-methoxyphenyl)acrylate.

Examples of the hindered amine-based light stabilizer include hindered amine compounds such as 2,2,6,6-tetramethyl-4-piperidylshearate, 1,2,2,6,6-pentamethyl-4-piperidylshearate, 2,2,6,6-tetramethyl-4-piperidylbenzoate, bis (2,2,6,6-tetramethyl-4-piperidyl)sebacate, bis(1,2,2,6,6-tetramethyl-4-piperidyl)sebacate, bis(l-octoxy-2,2,6,6-tetramethyl-4-piperidyl)sebacate, tetrakis(2,2,6,6-tetramethyl-4-piperidyl)-1,2,3,4-butanetetracarboxylate, tetrakis(1,2,2,6,6-pentamethyl-4-piperidyl)-1,2,3,4-butanetetracarboxylate, bis(2,2,6,6-tetramethyl-4-piperidyl)·di(tridecyl)-1,2,3,4-butane tetracarboxylate, bis(1,2,2,6,6-pentamethyl-4-piperidyl)·di(tridecyl)-1,2,3,4-buta netetracarboxylate, bis (1,2,2,4,4-pentamethyl-4-piperidyl)-2-butyl-2-(3,5-di-tert-butyl-4-hydroxybenzyl)malonate, 1-(2-hydroxyethyl)-2,2,6,6-tetramethyl-4-piperidinol/diethyl succinate polycondensate, 1,6-bis(2,2,6,6-tetramethyl-4-piperidylamino)hexane/2,4-dichloro-6-morpholino-s-triazine polycondensate, 1,6-bis(2,2,6,6-tetramethyl-4-piperidylamino)hexane/2,4-dichloro-6-tert-octylamino-s-triazine polycondensate, 1,5,8,12-tetrakis[2,4-bis(N-butyl-N-(2,2,6,6-tetramethyl-4-piperidyl)amino)-s-triazin-6-yl]-1,5,8,12-tetraazadodecane, 1,5,8,12-tetrakis[2,4-bis(N-butyl-N-(1,2,2,6,6-pentamethyl-4-piperidyl)amino)-s-triazin-6-yl]-1,5,8-12-tetraazadodecane, 1,6,11-tris[2,4-bis(N-butyl-N-(2,2,6,6-tetramethyl-4-piperidyl)amino)-s-triazin-6-yl] aminoundecane, and 1,6,11-tris[2,4-bis (N-butyl-N-(1,2,2,6,6-pentamethyl-4-piperidyl)amino)-s-triazin-6-yl] aminoundecane.

Examples of the near-infrared absorber include a polymethine-based dye (cyanine dye), an indolinocyanine-based dye, a phthalocyanine-based dye, a naphthalocyanine-based dye, a naphthol metal complex-based dye, a squarylium dye, a triazo dye, a dithiol metal complex salt-based dye, a pyrylium dye, a thiapyrylium dye, an indoaniline dye, an azoanthraquinone dye, a naphthoquinone dye, an anthroquinone dye, bis(dithiolene) dye, a triphenylmethane dye, an aminium (aluminum) dye, and a diimonium-based dye. Examples of the near-infrared absorber further include inorganic absorbers such as carbon black, a tin oxide doped with antimony oxide or indium oxide, and an oxide, a carbide, or a boride of metals belonging to Groups IVA, VA, or VIA of the periodic table.

Examples of the nucleating agent include metal salts of benzoic acids such as aluminum p-tert-butylbenzoate and sodium benzoate, aromatic phosphoric acid ester metal salts such as bis(2,4-di-tert-butylphenyl)phosphate ester sodium, methylenebis(2,4-di-tert-butylphenyl)phosphate ester sodium, and bis[methylenebis(2,4-di-tert-butylphenyl)phosphate ester]hydroxyaluminum and a mixture of an aromatic phosphoric acid ester metal salt and an alkali metal compound, dibenzylidene sorbitols such as dibenzylidene sorbitol, bis(methylbenzylidene)sorbitol, bis(p-ethylbenzylidene)sorbitol, and bis(dimethylbenzylidene sorbitol), and amide compounds such as an amino acid metal salt, a rosin acid metal salt, N,N',N"-tris[2-methylcyclohexyl]-1,2,3-propanetricarboxamide, N,N',N"-tricyclohexyl-1,3,5-benzenetricarboxamide, N,N'-dicyclohexylnaphthalenedicarboxamide, and 1,3,5-tri (dimethylisopropoylamino)benzene.

Examples of the antistatic agent include: cationic antistatic agents such as a fatty acid quaternary ammonium ion salt and a polyamine quaternary salt; anionic antistatic agents such as a higher alcohol phosphate ester salt, a higher alcohol EO adduct, polyethylene glycol fatty acid ester, an anionic alkyl sulfonate salt, a higher alcohol sulfate ester salt, a higher alcohol ethylene oxide adduct sulfate ester salt, and a higher alcohol ethylene oxide adduct phosphate ester salt; nonionic antistatic agents such as polyhydric alcohol fatty acid ester, polyglycol phosphate ester, and polyoxyethylene alkylallyl ether; and an amphoteric alkylbetaine such as betaine alkyldimethylaminoacetate, amphoteric antistatic agents such as imidazoline-type amphoteric activator, and a polymeric antistatic agent containing a block polymer having an ionomer and polyethylene glycol as a hydrophilic moiety.

Examples of the lubricant include: hydrocarbon lubricants such as liquid paraffin, paraffin wax, and polyethylene wax; aliphatic lubricants such as stearyl alcohol, stearic acid, and 12-hydroxystearic acid; amide-based lubricants such as stearic acid amide, oleic acid amide, erucic acid amide, methylenebisstearic acid amide, and ethylene stearic acid amide; metal soap-based lubricants such as calcium stearate, zinc stearate, magnesium stearate, lead stearate, aluminum stearate, barium stearate, a barium stearate/zinc stearate complex, and a zinc stearate/calcium stearate complex; and ester-based lubricants such as hardened oil, glycerin monostearate, butyl stearate, pentaerythritol stearate, and stearyl stearate.

Examples of the plasticizer include phthalic acid ester, a dibasic acid ester, chlorinated paraffin, polyester, an epoxidized ester, a phosphoric acid ester, and trimellitic acid ester.

Examples of the light absorbing dye include a cyanine-based, a quinoline-based, a coumarin-based, a thiazole-based, an oxonol-based, an azulene-based, a squarylium-based, an azomethine-based, an azo-based, a benzylidene-based, a xanthene-based, a phthalocyanine-based, and a dithiol metal complex-based compounds.

Examples of the filling agent include calcium carbonate, calcium oxide, calcium hydroxide, zinc hydroxide, zinc carbonate, zinc sulfide, magnesium oxide, magnesium hydroxide, magnesium carbonate, aluminum oxide, aluminum hydroxide, a metal silicate salt such as sodium alumina silicate, hydrocalumite, aluminum silicate, magnesium silicate, and calcium silicate, zeolite, activated clay, talc, clay, red iron oxide, asbestos, antimony trioxide, silica, glass beads, mica, sericite, glass flake, asbestos, wollastonite, potassium titanate, PMF (mineral fiber), gypsum fiber, zonolite, a magnesium hydroxide sulfate hydrate (MOS, a fibrous magnesium compound), phosphate fiber, glass fiber, carbon fiber, aramid fiber, and cellulose nanofiber.

As the pigment, commercially available pigments may be used, and examples thereof include: Pigment Red 1, 2, 3, 9, 10, 17, 22, 23, 31, 38, 41, 48, 49, 88, 90, 97, 112, 119, 122, 123, 144, 149, 166, 168, 169, 170, 171, 177, 179, 180, 184, 185, 192, 200, 202, 209, 215, 216, 217, 220, 223, 224, 226, 227, 228, 240, 254; Pigment Orange 13, 31, 34, 36, 38, 43, 46, 48, 49, 51, 52, 55, 59, 60, 61, 62, 64, 65, and 71; Pigment Yellow 1, 3, 12, 13, 14, 16, 17, 20, 24, 55, 60, 73, 81, 83, 86, 93, 95, 97, 98, 100, 109, 110, 113, 114, 117, 120, 125, 126, 127, 129, 137, 138, 139, 147, 148, 150, 151, 152, 153, 154, 166, 168, 175, 180, and 185; Pigment Green 7, 10, and 36; Pigment Blue 15, 15:1, 15:2, 15:3, 15:4, 15:5, 15:6, 22, 24, 56, 60, 61, 62, and 64; and Pigment Violet 1, 19, 23, 27, 29, 30, 32, 37, 40, and 50.

Examples of the dyestuff include an azo dyestuff, an anthraquinone dyestuff, an indigoid dyestuff, a triarylmethane dyestuff, a xanthene dyestuff, an alizarin dyestuff, an acridine dyestuff, a stilbene dyestuff, a thiazole dyestuff, a naphthol dyestuff, a quinoline dyestuff, a nitro dyestuff, an indamine dyestuff, an oxazine dyestuff, a phthalocyanine dyestuff, and a cyanine dyestuff.

Examples of the metal soap include metals such as lithium, sodium, potassium, magnesium, calcium, aluminum, hydroxyaluminum, barium, and zinc, and salts of saturated or unsaturated fatty acid salts such as lauric acid, myristic acid, palmitic acid, stearic acid, behenic acid, and oleic acid.

The processing aid can be appropriately selected from known processing aids, but an acrylic acid-based processing aid is preferable. Examples of the processing aids include: a homopolymer or copolymer of an alkyl methacrylate such as methyl methacrylate, ethyl methacrylate, or butyl methacrylate; a copolymer of the alkyl methacrylate with an alkyl acrylate such as methyl acrylate, ethyl acrylate, or butyl acrylate; a copolymer of the alkyl methacrylate with an aromatic vinyl compound such as styrene, α-methyl styrene, or vinyl toluene; and a copolymer of the alkyl methacrylate with a vinyl cyan compound such as acrylonitrile or methacrylonitrile.

Examples of the flame retardant and the flame retardant aid include a triazine ring-containing compound described later, a metal hydroxide, other inorganic phosphorus, a halogen-based flame retardant, a silicone-based flame retardant, a phosphoric acid ester-based flame retardant, a condensed phosphoric acid ester-based flame retardant, an intumescent-based flame retardant, an antimony oxide such as antimony trioxide, other inorganic flame retardant aids, and an organic flame retardant aid.

Examples of the triazine ring-containing compound include melamine, ammeline, benzguanamine, acetoguanamine, phthalodiguanamine, melamine cyanurate, melamine pyrophosphate, butylene diguanamine, norbornene diguanamine, methylene diguanamine, ethylene dimelamine, trimethylene dimelamine, tetramethylene dimelamine, hexamethylene dimelamine, and 1,3-hexylene dimelamine.

Examples of the metal hydroxide include magnesium hydroxide, aluminum hydroxide, calcium hydroxide, barium hydroxide, zinc hydroxide, and KISUMA 5A (magnesium hydroxide, manufactured by Kyowa Chemical Industry Co., Ltd.).

Examples of the phosphoric acid ester-based flame retardant include trimethyl phosphate, triethyl phosphate, tributyl phosphate, tributoxyethyl phosphate, trischloroethyl phosphate, trisdichloropropyl phosphate, triphenyl phosphate, tricresyl phosphate, and cresyl diphenyl phosphate, trixylenyl phosphate, octyldiphenyl phosphate, xylenyldiphenyl phosphate, trisisopropylphenyl phosphate, 2-ethylhexyldiphenyl phosphate, tert-butylphenyldiphenyl phosphate, bis (tert-butylphenyl)phenyl phosphate, tris-(tert-butylphenyl) phosphate, isopropylphenyldiphenyl phosphate, bis-(isopropylphenyl)diphenyl phosphate, and tris-(isopropylphenyl) phosphate.

Examples of the condensed phosphoric acid ester-based flame retardant include 1,3-phenylenebis(diphenyl phosphate), 1,3-phenylenebis(dixylenyl phosphate), bisphenol A bis(diphenyl phosphate), and examples of the intumescent-based flame retardant include ammonium salts or amine salts of (poly)phosphoric acids such as ammonium polyphosphate, melamine polyphosphate, piperazine polyphosphate, ammonium pyrophosphate, melamine pyrophosphate, and piperazine pyrophosphate.

Examples of the other inorganic flame retardant aids include inorganic compounds such as titanium oxide, aluminum oxide, magnesium oxide, and talc, and surface-treated products thereof. For example, various commercially available products such as TIPAQUER-680 (titanium oxide, manufactured by Ishihara Sangyo Kaisha, Ltd.) and KYOWAMAG 150 (magnesium oxide, manufactured by Kyowa Chemical Industry Co., Ltd.) can be used.

Examples of other organic flame retardant aids include pentaerythritol and dipentaerythritol.

The zeolite compound described above is an alkali or alkaline earth metal aluminosilicate having a unique three-dimensional zeolite crystal structure. The representative examples thereof include an A-type, an X-type, a Y-type, and a P-type zeolite, monodenite, analsite, a sodalite group aluminosilicate, clinobuchilorite, erionite, and chabazite. Any of a hydrous substance having crystal water of these zeolite compounds (so-called zeolite water) or an anhydrous substance from which the crystal water has been removed may be used. As the zeolite compound, those having a particle size of 0.1 to 50 μm can be used, and one having a particle size of 0.5 to 10 μm is particularly preferable.

Examples of the foaming agent include decomposable organic foaming agents such as azodicarbonamide, azobisisobutyronitrile, p,p'-oxybisbenzenesulfonylhydrazide, n,n'-dinitrosopentamethylenetetramine, p-toluenesulfonylsemicarbazide, and trihydrazotriazine, and decomposable inorganic foaming agents such as sodium bicarbonate, ammonium carbonate, ammonium bicarbonate, ammonium nitrite, azide compound, and sodium borohydride.

Examples of the (heavy) metal deactivator include salicylamide-1,2,4-triazol-3-yl, bissalicylic acid hydrazide, dodecanedioylbis(2-(2-hydroxybenzoyl)hydrazide), and bis(3-(3,5-di-tert-butyl-4-hydroxyphenyl)propionic acid)hydrazide.

Examples of the cross-linking agent include benzoylperoxide, di-tert-butylperoxide, dicumylperoxide, 2,5-dimethyl-2,5-di(tert-butylperoxy) hexane, 2,5-dimethyl-2,5-di(tert-butylperoxy) hexyne, 1,3-bis(tert-butylperoxyisopropyl)benzene-tert-butyl-hydroperoxide, cumene hydroperoxide, polysulfone azide, azidoformate, tetramethylisophthalyl di-tert-butylbisperoxide, tetramethylisophthalyl dicumylbisperoxide, alkanolamines such as diethanolamine and triethanolamine, hexamethylenediamine, and 4,4'-diaminodiphenylmethane.

Examples of the epoxy-based stabilizer include compounds having an aliphatic, aromatic, alicyclic, araliphatic, or heterocyclic structure and having an epoxy group as a side chain. The epoxy group is preferably attached to the residue of a molecule by an ether or ester bond as a glycidyl group or the epoxy group may be an N-glycidyl derivative of a heterocyclic amine, amide, or imide. Specific examples thereof include epoxidized soybean oil, epoxidized linseed oil, and epoxidized monoester. Examples of commercially available epoxy-based stabilizer include "ADEKA CIZER O-130P", "ADEKA CIZER O-180A", "ADEKA CIZER D-32", "ADEKA CIZER EP-13", and ADEKA CIZER FEP-13" (product names, manufactured by ADEKA CORPORATION).

As the matte agent, fine particles of silicon dioxide are preferable. Examples of the fine particles of silicon dioxide include AEROSIL R972, R972V, R974, R812, 200, 200V, 300, R202, OX50, and TT600 (manufactured by NIPPON AEROSIL CO., LTD.). AEROSIL 200V, AEROSIL R972V, and AEROSIL R812 are preferable since they have a large effect of lowering the coefficient of friction while keeping the haze of the film low.

Examples of the anti-fogging agent include glycerin fatty acid ester, alkyldiethanol amine, and alkyldiethanol amine fatty acid ester.

Examples of the plate-out preventing agent include silicon dioxide and a substance containing, as an active ingredient, an alkylene oxide adduct of a saponified ethylene-saturated carboxylic acid vinyl ester copolymer.

As the surface treatment agent, for example, a surface treatment agent including one or more kinds of aminosilane compounds and epoxy resins is preferably used.

Examples of the aminosilane compound include γ-aminopropyltriethoxysilane, γ-aminopropyltrimethoxysilane, and γ-(2-aminoethyl)aminopropyltrimethoxysilane.

Examples of the epoxy resin included in the surface treatment agent include a novolac-type epoxy resin and a bisphenol-type epoxy resin, and a novolac-type epoxy resin is preferably used. Examples of the novolac-type epoxy resin include polyfunctional epoxy resins such as a phenol novolac-type epoxy resin and a cresol novolac-type epoxy resin.

Further, in addition to the above aminosilane compound and epoxy resin, the surface treatment agent may be blended with components such as a urethane resin, an acrylic resin, an antistatic agent, a lubricant, and a water repellent, as long as the properties of the surface treatment agent are not impaired. Further, as other surface treatment agents, an epoxy resin other than the novolac-type and the bisphenol-type and a coupling agent can be mentioned.

The fluorescent whitening agent is a compound that promotes whiteness and bluishness of a molded article by a fluorescence action that absorbs ultraviolet rays of sunlight or artificial light, converts the absorbed ultraviolet rays into visible light of purple to blue colors, and radiate the visible light. Examples of the fluorescent whitening agent include: a benzoxazole-based compound C.I. Fluorescent Brightner 184; a coumarin-based compound C.I. Fluorescent Brightner 52; and a diaminostilbene disulphonic acid-based compound C.I. Fluorescent Brightner 24, 85, and 71.

Examples of the antifungal agent include organic antifungal agents such as a nitrogen-containing and sulfur-containing antifungal agent, an organic bromine-based antifungal agent, a nitrogen-containing antifungal agent, and arsenic-based antifungal agent, and inorganic antifungal agents such as a silver compound.

Examples of the antibacterial agent include, organic antibacterial agents such as compounds a chlorine-based, a phenol-based, an imidazole-based and a thiazole-based compound, and a quaternary ammonium compound, and inorganic antibacterial agents such as a zeolite-based, an apatite-based, a silica-alumina-based, a ceramic-based, a zirconium phosphate-based, a silica gel-based, a hydroxyapatite-based, and a calcium silicate-based compounds, where the zeolite-based antibacterial agent retains and contains metals such as silver and zinc.

Examples of the releasing agent include sodium montanate, potassium montanate, calcium montanate, and magnesium montanate.

The method for producing a resin composition of the present embodiment is not particularly limited, and any conventionally known method can be adopted.

One example of the method for producing a resin composition includes a method in which all components of the particulate ultraviolet absorber of the present embodiment, the synthetic resin described above, and other additive components as necessary are premixed using various mixers such as a tumbler and a Henschel mixer, and then melt-kneaded with a Banbury mixer, a roll, Brabender, a single-screw kneading extruder, a twin-screw kneading extruder, or a kneader.

Alternatively, the resin composition may be produced, without premixing all the components, by premixing only a part of the components, supplying the premixture to an extruder using a feeder, and performing melt-kneading. Further, the resin composition can also be produced by a method in which the resin composition obtained by mixing a part of the components in advance, supplying the mixture to an extruder, and performing me it-kneading is used as a master batch for melt-kneading, which is mixed again with other components.

In addition, the synthetic resin used in the mixing and kneading step may have a predetermined shape such as a powder shape and a pellet shape, or a fiber shape.

The resin composition of the present embodiment may be solid at room temperature or may have a constant shape such as a powder shape, a granule shape, a pellet shape, a briquette shape, and a tablet shape, or a sheet shape.

A molded article can be obtained by molding the resin composition of the present embodiment.

The molding method is not particularly limited and may be injection molding, extrusion molding, blow molding, rotational molding, vacuum molding, inflation molding, calendar molding, slash molding, dip molding, foam molding, or the like.

The molded articles can have various forms depending on the applications and may have various shapes such as a resin plate, a sheet, a film, a container (bottle, tray, bag), a fiber, and various molded products.

Further, in the resin composition of the present embodiment, each component of the particulate ultraviolet absorber of the present embodiment, the above-described synthetic resin used as a binder resin, as necessary, and other additive components as necessary may be dissolved in a solvent to be a varnish resin (a varnish resin composition that is liquid at room temperature). As the solvent, an organic solvent or an aqueous solvent can be used. The resin varnish may be used as an emulsion in which a powdery ultraviolet absorber is dispersed by using an emulsifier as necessary.

In the method for preparing the resin varnish, the order of mixing each component is not particularly limited, all the components may be mixed at the same time, the synthetic resin may be mixed in advance with the particulate ultraviolet absorber of the present embodiment and other additive components, a plurality of components prepared in advance may be mixed with other components, or a plurality of components prepared in advance may be further mixed with each other.

The resin varnish can be processed into a film or a sheet by using, for example, a cast film method. The resin varnish can also be used as a coating material for coating a predetermined base material.

The resin composition of the present embodiment can be used in a wide range of industrial fields such as electricity, electronics, communications, agriculture, forestry and fisheries, mining, construction, food, textiles, clothing, medical care, coal, oil, rubber, leather, automobiles, precision equipment, wood, building materials, civil engineering, furniture, printing, and musical instruments.

More specific examples of the applications include office work or OA devices such as a printer, a PC, a word processor, a keyboard, a small information terminal (Personal Digital Assistant (PDA)), a telephone, a copier, a facsimile, an electronic cash register (ECR), a calculator, an electronic notebook, a card, a holder, and a stationary, home appliances such as a laundry machine, a refrigerator, a vacuum cleaner, a microwave oven, lighting equipment, a game machine, an iron, and a kotatsu, AV devices such as a TV, a VTR, a video camera, a radio-cassette recorder, a tape recorder, a mini disk, a CD player, a speaker, and a liquid crystal display, an electric or electronic components and communication devices such as a connector, a relay, a capacitor, a switch, a printed circuit board, a coil bobbin, a semiconductor encapsulation material, a LED encapsulation material, an electric wire, a cable, a transformer, a deflection yoke, a distribution board, and a clock, and an interior and exterior material for an automobile, a film for plate making, an adhesive film, a bottle, a food container, a food packaging film, a pharmaceutical or medical wrap film, a product packaging film, an agricultural film, an agricultural sheet, and greenhouse film.

Other more specific examples of the applications include materials for an automobile, a vehicle, a ship, aircraft, a building, a house, construction, and civil engineering, such as a seat (a filling material, an outer material, and the like), a belt, a ceiling covering, a compatible top, an armrest, a door trim, a rear package tray, a carpet, a mat, a sun visor, a foil cover, a mattress cover, an airbag, an insulation material, a sling, a sling band, a wire coating material, an electrical insulation material, a paint, a coating material, an upholstery material, a floor material, a corner wall, a carpet, wallpaper, a wall covering, an exterior material, an interior material, a roofing material, a deck material, a wall material, a column material, a flooring material, a fence material, a skeleton and molding, a window and door profile, a shingle, siding, a terrace, a balcony, a soundproof board, a heat insulation board, and a window material, household goods and sports goods such as clothing, a curtain, a sheet, a non-woven fabric, plywood, fibrous plywood, a carpet, an entrance mat, a sheet, a bucket, a hose, a container, glasses, a bag, a case, a goggle, skis, a racket, a tent, and a musical instrument. In addition to these, a paint, a cosmetic, and the like can be mentioned.

Additional applications can be also mentioned as follows: containers for medicines such as a drug, a vitamin, a drink, and an eye drop; containers for cosmetics such as a lotion, an emulsion, and a sunscreen; containers for beverage such as a food container, liquor, wine, beer, fruit juice, soft drink, tea, black tea, and coffee; and containers for daily necessities such as a shampoo, a conditioner, a mouthwash, a toothpaste, and a disinfectant.

Further, the resin composition of the present embodiment is not particularly limited but can be suitably used as an optical material such as an optical film or an optical sheet by molding the resin composition into a sheet or a film. For example, the resin composition as the optical material can be used for image display devices such as a liquid crystal display device (LCD), a plasma display panel (PDF), an electroluminescence display (ELD), a cathode ray tube display device (CRT), a fluorescent display tube, and a field emission display as the optical film or the optical sheet. The resin composition is particularly useful as optical films such as a liquid crystal display device using an organic material having inferior ultraviolet resistance for a display element, an optical correction film for an organic EL display, and a light emitter protective film.

For applications in the liquid crystal display device, a polarizing plate protective film or protective sheet, a phase difference film, a viewing angle expansion film, an antiglare film, a brightness enhancement film, a light diffusion film, and light diffusion sheet, a lens film, and lens sheet, an anti-fogging film, an antistatic film, an optical correction film, an antireflection film, a color adjustment film, and a light guide plate can be mentioned. Particularly, the resin composition of the present embodiment can be suitably used for an optical film or an optical sheet provided on the outer surface side of a polarizing plate which is in contact with a liquid crystal display element, or a polarizing plate protective film or an optical sheet.

The embodiments of the present invention have been described as above, but these are examples of the present invention, and various configurations other than the above-described configurations can be adopted.

Hereinafter, the present invention will be described in detail with reference to Examples, but the present invention is not limited to the description of Examples.

[Preparation of Particulate Ultraviolet Absorber]

Example 1

2,4,6-tris[2-hydroxy-3-methyl-4-hexyloxyphenyl] triazine was synthesized by the following procedure.

In a 300 ml four-necked flask, 10.00 g of 2,4,6-tris(2,4-dihydroxy-3-methylphenyl) triazine, 22.68 g of sodium hydroxide, 80.00 g of dimethylformamide, and 11.07 g of 1-bromo-hexane were added, the temperature was raised to 80° C., and the reaction was performed for 9 hours. After performing a neutralization treatment with hydrochloric acid, washing with water, desolvation under reduced pressure, and recrystallization of the residue from toluene:isopropyl alcohol=1:1 were performed, and crystals were obtained. Thereafter, the melted target substance (crystal) was dropped onto a metal plate and cooled to obtain flakes (melting solidification treatment). By pulverizing the obtained flakes in a mortar, 11.89 g (yield: 76%) of pale yellow powder having a melting point of 145° C. was obtained.

The obtained compound (pale yellow powder) was subjected to $^1$H-NMR measurement. From the following analysis results, the pale yellow powder obtained was identified as a powdery compound (particulate ultraviolet absorber) represented by the following formula No. 1.

Example 2

The flakes obtained in Example 1 were roughly pulverized and classified to obtain a compound (particulate ultraviolet absorber) represented by the above formula No. 1 and having a granule form.

Example 3

2-(4-(4,6-diphenyl-1,3,5-triazin-2-yl)-3-hydroxyphenoxy)ethyl 2-ethylhexanoate was synthesized by the following procedure.

In a 300 ml four-neck flask, 10.00 g of 2-(4,6-diphenyl-1,3,5-triazin-2-yl)-5-(2-hydroxyethoxy) phenol, 0.25 g of paratoluenesulfonic acid monohydrate, 70.00 g of toluene, and 4.12 g of 2-ethylhexanoic acid were added, and the mixture was reacted under reflux for 10 hours. After washing the reaction product with water, crystals were obtained by recrystallization from toluene:isopropyl alcohol=1:2. Thereafter, the melted target substance (crystal) was dropped onto a metal plate and cooled to obtain flakes (melting solidification treatment). By pulverizing the obtained flakes in a mortar, 9.56 g (yield: 72%) of pale yellow powder having a melting point of 108° C. was obtained.

The obtained compound (pale yellow powder) was subjected to $^1$H-NMR measurement. From the following analysis results, the pale yellow powder obtained was identified as a powdery compound represented by the following formula No. 2.

The obtained flakes were roughly pulverized and classified to obtain a compound (particulate ultraviolet absorber) represented by the above formula No. 2 and having a granule form.

Compound No. 1

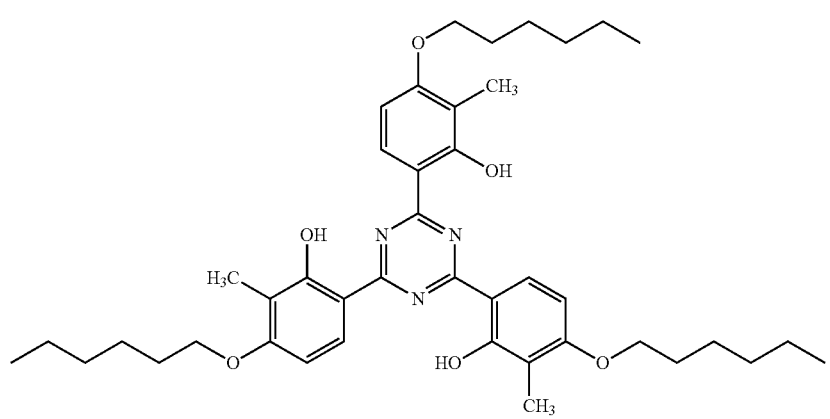

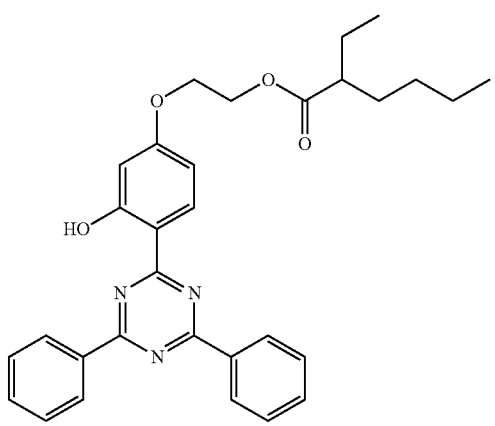

Compound No. 2

Comparative Example 1

The crystals obtained in Example 1 were dissolved in toluene and allowed to be left at room temperature for 2 weeks to obtain particulate crystals. Then, classification was performed to obtain a powdery compound (particulate ultraviolet absorber) represented by the above formula No. 1 and having a uniform particle size.

Comparative Example 2

The crystals obtained in Example 1 were pulverized in a mortar without performing the melting solidification treatment to obtain a powdery compound (particulate ultraviolet absorber) represented by the above formula No. 1.

The particulate ultraviolet absorber obtained as described above was evaluated based on the following evaluation items. Table 1 shows the evaluation results.

(Compressibility)

Using a powder characteristics evaluation device (Multi-tester MT-02, manufactured by Seishin Enterprise Co., Ltd.,) and a cylindrical "container" having a diameter of 5 cm and a volume of 100 cm$^3$, a bulk density of the obtained particulate ultraviolet absorber (sample) was measured.

First, the container was gently filled with the sample so that the sample became heaped, and the excess sample above the container surface was leveled off, and the weight of the sample roughly filled in the container was measured. At this time, the loose bulk density (g/cm$^3$) was calculated from the weight (g) of the sample roughly filled into the container by dividing with 100 (cm$^3$).

Subsequently, a cap was attached to the container, tapping was performed from a height of 18 mm under the condition of 180 times of tapping, and then excess powder above the container surface was leveled off and the weight was measured. At this time, the tight bulk density (g/cm$^3$) was calculated from the weight (g) of the sample filled into the container after tapping by dividing with 100 (cm$^3$).

In addition, in a case where the loose bulk density was denoted by D1 and the tight bulk density was denoted by D2, the compressibility (%) was calculated based on expression: $[(D2-D1)/D2]\times100$. Table 1 shows the evaluation results.

(Feeding Property)

1 kg of the obtained particulate ultraviolet absorber was charged into a hopper and then discharged (feeding property test) for 30 minutes under the condition of a feeder discharge rate of 0.3 kg/h by using a gravimetric feeder (manufactured by Coperion K-Tron, length: 25 cm×outer diameter: 1.4 cm, groove width: 2.0 cm, groove depth: 0.3 cm, twin spiral-type biaxial screw).

Quantitativity

The amount discharged from the gravimetric feeder (feeder amount) was temporally measured at intervals of 10 minutes. A case where the variation in the feed amount was small was indicated as A, and a case where the variation in the feed amount was large was indicated as C.

Long Run Property

The above feed test was carried out in the same manner except that the discharge time condition was changed from 30 minutes to 3 hours. A case where the discharge was continued for 3 hours was indicated as A, and a case where the operation was stopped before the lapse of 3 hours was indicated as C.

(Compression Granulation Property)

The obtained particulate ultraviolet absorber was compression-granulated under the conditions of a roll gap of 3.2 mm and a roll rotation speed of 14 rpm to obtain plate-shaped granules having a plate thickness of 4 mm by using a roller compactor (Granulator M-25 type, manufactured by Hosokawa Micron Group). The obtained plate-shaped granules were pulverized, the coarse powder was removed with a 5-mesh vibrating sieve, fine powder was subsequently removed (particle grading) with a 24-mesh vibrating sieve, and then a plate-shaped granulated product remained on a 24-mesh vibrating comb was obtained.

The appearance of the obtained granulated product was observed, and the disintegration degree of the granulated product was evaluated based on the following criteria.

A case where the disintegration was not observed in 10 granulated products out of 10 granulated products was indicated as A, a case where the partial disintegration was observed in 1 or more and 4 or less granulated products out of 10 granulated products was indicated as B, and a case where the partial or whole disintegration was observed in 5 or more granulated products out of 10 granulated products was indicated as C.

TABLE 1

|  | Unit | Comparative Example 1 | Example 2 | Example 1 | Example 3 | Comparative Example 2 |
|---|---|---|---|---|---|---|
| Compressibility | % | 4.7 | 6.6 | 20.3 | 38.5 | 42.9 |
| Loose bulk density | g/cm$^3$ | 0.41 | 0.57 | 0.47 | 0.48 | 0.20 |
| Tight bulk density | g/cm$^3$ | 0.43 | 0.61 | 0.59 | 0.78 | 0.35 |
| Feeding Quantitativity property | | A | A | A | A | C |
| Long run property | | A | A | A | A | C |
| Compression granulation property | | C | A | A | A | C |

Further, the X-ray diffraction analysis was performed on the obtained particulate ultraviolet absorber of Examples 1 to 3 and Comparative Example 2. The evaluation results are shown in Tables 2 to 5.

TABLE 2

|  | Unit | Example 1 | Example 2 | Example 3 | Comparative Example2 |
|---|---|---|---|---|---|
| Diffraction angle 2θ of maximum peak | ° | 5.58 | 5.58 | 5.74 | 6.73 |
| Half-width of maximum peak | ° | 0.18 | 0.18 | 0.12 | 0.20 |

(X-Ray Diffraction)
Powder X-ray diffraction measurement was performed on the obtained particulate ultraviolet absorber using Ultima IV (manufactured by Rigaku Corporation) under the following measurement conditions.
(Measurement Condition)
X-ray tube lamp: CuKα ray (CuKα1=1.540562 Å, CuKα2=1.544398 Å, CuKα2 not removed)
Tube voltage/tube current: 40 kV/40 mA
Attachment: multipurpose thin film sample stand
Monochromator: fixed
Filter: none
Divergence slit: ⅔°
Divergence vertical restriction slit: 10 mm
Scattering slit: 1.17 mm
Light receiving slit: 0.3 mm
Scan type: continuous scan
Scan speed: 4°/min
Sampling width: 0.02°
Scanning axis: 2θ/ω
Scanning range: =3° to 90°

The result of the powder X-ray diffraction analysis of the particulate ultraviolet absorber of Example 1 is shown in FIG. 1. Table 3 shows the diffraction angle 2θ, the d value, and the relative intensity corresponding to each peak in FIG. 1. In Table 3, "deg" indicates "°", and the threshold of the peak intensity was set to 1/100 of the maximum peak.

TABLE 3

| No. | 2θ (deg) | d (Å) | Relative intensity |
|---|---|---|---|
| 1 | 5.58 | 15.81 | 100 |
| 2 | 7.23 | 12.21 | 3 |
| 3 | 10.79 | 8.19 | 2 |
| 4 | 12.06 | 7.33 | 2 |
| 5 | 12.34 | 7.17 | 2 |
| 6 | 14.35 | 6.17 | 2 |
| 7 | 15.53 | 5.70 | 8 |
| 8 | 15.88 | 5.57 | 3 |
| 9 | 16.18 | 5.47 | 3 |
| 10 | 16.62 | 5.33 | 2 |
| 11 | 17.12 | 5.17 | 5 |
| 12 | 20.11 | 4.41 | 3 |
| 13 | 20.82 | 4.26 | 2 |
| 14 | 21.69 | 4.09 | 7 |
| 15 | 22.10 | 4.02 | 18 |
| 16 | 23.23 | 3.83 | 2 |
| 17 | 23.79 | 3.74 | 7 |
| 18 | 24.41 | 3.64 | 8 |
| 19 | 26.11 | 3.41 | 3 |
| 20 | 26.80 | 3.32 | 3 |
| 21 | 28.09 | 3.17 | 4 |

As a result of the powder X-ray diffraction analysis, the X-ray diffraction pattern of the particulate ultraviolet absorber of Example 2 was substantially the same as the X-ray diffraction pattern of the particulate ultraviolet absorber of Example 1.

Figure 2:
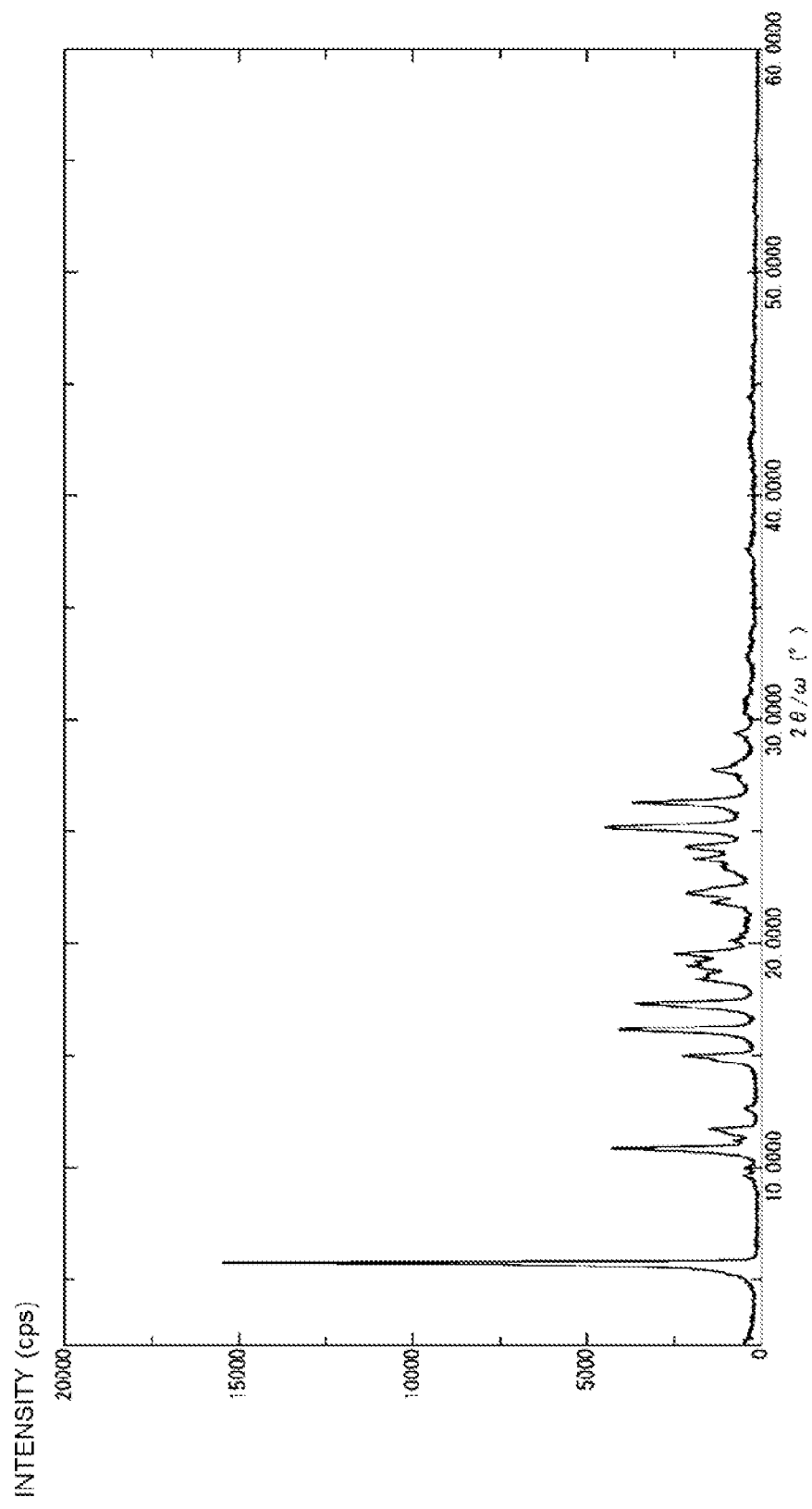
FIG. 2 is an X-ray diffraction pattern of a particulate ultraviolet absorber of Example 3.

The result of the powder X-ray diffraction analysis of the particulate ultraviolet absorber of Example 3 is shown in FIG. 2. Table 4 shows the diffraction angle 2θ, the d value, and the relative intensity corresponding to each peak in FIG. 2. In Table 4, the threshold of the peak intensity was set to 1/100 of the maximum peak.

However, the same procedure as in Example 1 was carried out except that the following conditions were adopted as the measurement conditions for the powder X-ray diffraction measurement in Example 3.
Divergence slit: ½°
Divergence vertical restriction slit: 10 mm
Scattering slit: 0.93 mm
Scanning range: =2° to 60°

TABLE 4

| No. | 2θ (deg) | d (Å) | Relative intensity |
|---|---|---|---|
| 1 | 5.74 | 15.39 | 100 |
| 2 | 9.62 | 9.19 | 2 |
| 3 | 9.98 | 8.85 | 2 |
| 4 | 10.87 | 8.13 | 26 |
| 5 | 11.69 | 7.56 | 8 |
| 6 | 12.61 | 7.02 | 2 |
| 7 | 15.01 | 5.90 | 11 |
| 8 | 16.16 | 5.48 | 25 |
| 9 | 17.34 | 5.11 | 20 |
| 10 | 18.40 | 4.82 | 9 |
| 11 | 19.03 | 4.66 | 9 |
| 12 | 19.49 | 4.55 | 11 |
| 13 | 20.07 | 4.42 | 3 |
| 14 | 21.81 | 4.07 | 6 |
| 15 | 22.28 | 3.99 | 11 |
| 16 | 23.37 | 3.80 | 3 |
| 17 | 23.78 | 3.74 | 8 |
| 18 | 24.26 | 3.67 | 10 |
| 19 | 25.15 | 3.54 | 25 |
| 20 | 26.29 | 3.39 | 21 |
| 21 | 27.33 | 3.26 | 2 |
| 22 | 27.72 | 3.22 | 7 |
| 23 | 28.06 | 3.18 | 2 |
| 24 | 29.44 | 3.03 | 3 |

Figure 3:
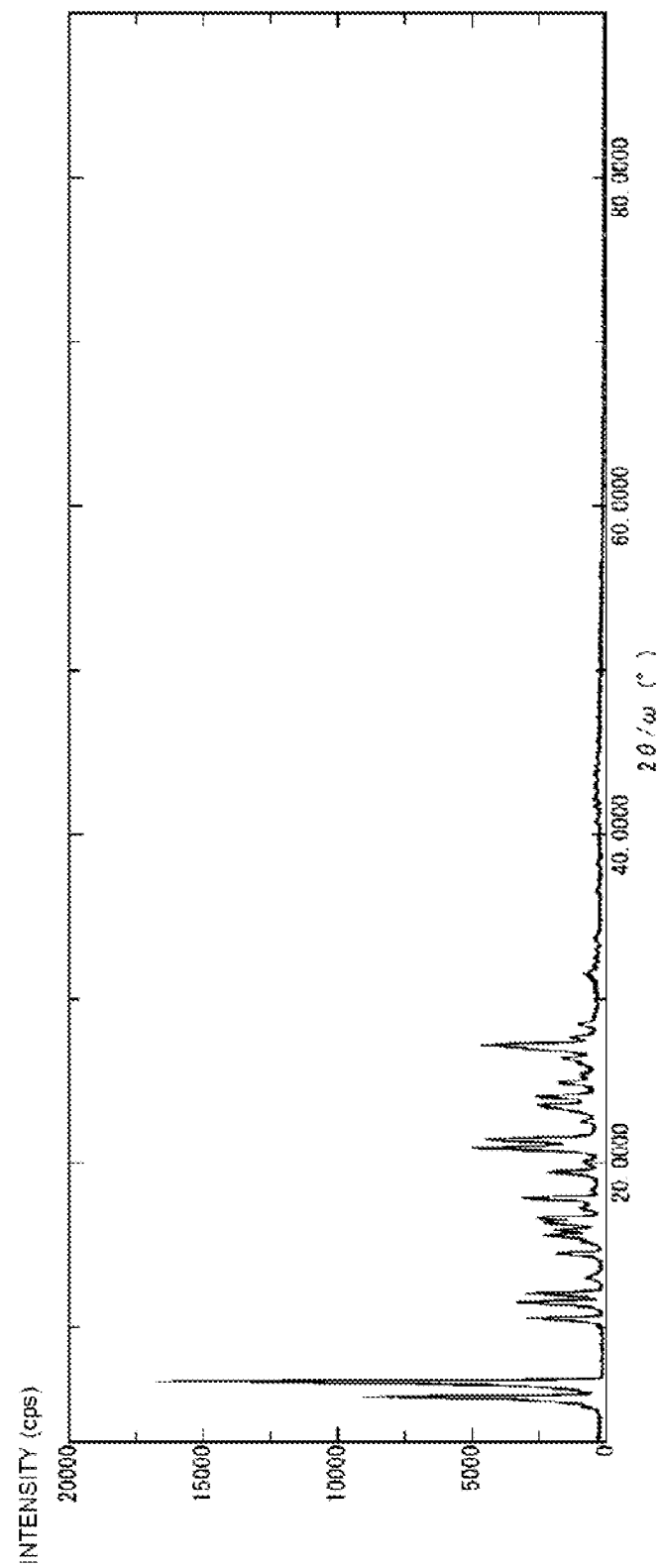
FIG. 3 is an X-ray diffraction pattern of a particulate ultraviolet absorber of Comparative Example 2.

The result of the powder X-ray diffraction analysis of the particulate ultraviolet absorber of Comparative Example 2 is shown in FIG. 3. Table 5 shows the diffraction angle 2θ, the d value, and the relative intensity corresponding to each peak in FIG. 3. In Table 5, the threshold of the peak intensity was set to 1/100 of the maximum peak.

TABLE 5

| No. | 2θ (deg) | d (Å) | Relative intensity |
|---|---|---|---|
| 1 | 5.78 | 15.26 | 52 |
| 2 | 6.73 | 13.12 | 100 |
| 3 | 10.55 | 8.38 | 15 |
| 4 | 11.52 | 7.67 | 19 |
| 5 | 12.07 | 7.33 | 16 |
| 6 | 12.99 | 6.81 | 3 |
| 7 | 14.51 | 6.10 | 10 |
| 8 | 15.28 | 5.79 | 3 |
| 9 | 15.60 | 5.67 | 12 |
| 10 | 15.93 | 5.56 | 9 |
| 11 | 16.37 | 5.41 | 11 |
| 12 | 16.68 | 5.31 | 15 |
| 13 | 17.39 | 5.10 | 3 |
| 14 | 17.89 | 4.95 | 17 |
| 15 | 19.45 | 4.56 | 11 |
| 16 | 20.05 | 4.42 | 3 |
| 17 | 20.90 | 4.25 | 25 |

TABLE 5-continued

| No. | 2θ (deg) | d (Å) | Relative intensity |
|---|---|---|---|
| 18 | 21.43 | 4.14 | 24 |
| 19 | 22.58 | 3.93 | 3 |
| 20 | 23.53 | 3.78 | 11 |
| 21 | 24.08 | 3.69 | 12 |
| 22 | 24.95 | 3.57 | 7 |
| 23 | 25.40 | 3.50 | 2 |
| 24 | 26.40 | 3.37 | 6 |
| 25 | 27.20 | 3.28 | 23 |
| 26 | 27.69 | 3.22 | 5 |
| 27 | 28.43 | 3.14 | 4 |
| 28 | 31.52 | 2.84 | 3 |

[Preparation of Resin Composition]

(Production of Film)

A resin composition was prepared by dissolving a mixture of 0.2 parts by mass of the obtained particulate ultraviolet absorber of each Example in 230 parts by mass of a solvent (toluene/cyclohexane=9/1) with respect to 100 parts by mass of a synthetic resin (polycarbonate resin: product name E-2000, manufactured by Mitsubishi Engineering Plastics Corporation). A film having a thickness of 40 μm was produced from the obtained resin composition by a casting method to obtain a square film test piece having a side of 2 cm.

The obtained film test piece was subjected to the measurement for the retention rates (%) of the total light transmittance (%) after 240, 360, and 480 hours with a sunshine weather meter (83° C., no rain, carbon arc light source), and the light resistance was evaluated.

From the result that the retention rates (%) after 240, 360, and 480 hours exhibited high values, it has been found that excellent light resistance can be realized by using the particulate ultraviolet absorber of each Example.

It has been also found that similarly excellent light resistance can be realized in a case where a methacrylic resin, a norbornene resin, a polyethylene terephthalate resin, or a polystyrene resin was used as the synthetic resin instead of the polycarbonate resin.

(Production of Container)

0.3 parts by mass of the obtained particulate ultraviolet absorber of each Example, with respect to 100 parts by mass of polyethylene terephthalate (intrinsic viscosity: 0.8 dL/g), was added and mixed to obtain a resin composition. The obtained resin composition was dried in a gear oven at 160° C. for 4 hours and then molded into a preform (outer diameter: 25 mm, weight: 23 g) by an injection molding machine at an injection molding temperature of 280° C. Next, the obtained preform was blow-molded with biaxial stretching at a mold temperature of 130° C. to produce a plastic bottle having a capacity of 500 mL and a thickness of 0.7 mm. The obtained plastic bottle was subjected to the measurement for the transmittance of visible light having a wavelength of 500 nm and the transmittance of ultraviolet light having a wavelength of 400 nm. From the results that the transmittance at a wavelength of 500 nm was high and the transmittance at a wavelength of 400 nm was low, it has been found that the obtained plastic bottle (container) efficiently absorbs ultraviolet rays and sufficiently achieve visible light transmittance.

(Production of Coating Material)

Ultraviolet Absorbing Layer 0.5 parts by mass of the particulate ultraviolet absorber of each of the obtained Examples, with respect to 100 parts by mass of a norbornene resin (product name: ARTONE 5023, manufactured by JSR Corporation), was mixed with 2,000 parts by mass of dichloromethane as a solvent and a resin solution (resin composition) was obtained. The obtained resin solution was cast on a surface-polished glass plate using a bar coater, preliminarily dried at 50° C. for 20 minutes, and dried at 90° C. for 30 minutes to produce a film having a thickness of 80 to 90 μm, and a square film test piece (ultraviolet absorbing layer) having a side of 2 cm was obtained.

Production of NIR Absorption Layer

A resin solution consisting of 0.3 parts by mass of a diimonium compound (product name: IRG-068, manufactured by Nippon Kayaku Co., Ltd.) as a near-infrared absorber and 2,000 parts by mass of dichloromethane as a solvent, with respect to 100 parts by mass of a norbornene resin (product name: ARTONE 5023, manufactured by JSR Corporation), was cast on the surface-polished glass plate by using a bar coater, preliminarily dried at 50° C. for 20 minutes, and dried at 90° C. for 30 minutes to produce a film having a thickness of 50 to 60 μm, and a square film test piece having a side of 2 cm was obtained.

The test piece obtained by superimposing the obtained NIR absorbing layer and the ultraviolet absorbing layer was exposed for 360 hours (or 540 hours) with a sunshine weathermeter (manufactured by Suga Test Instruments Co., Ltd.; 83° C., no rain, carbon arc light source) so that the test piece was exposed to test light from the ultraviolet absorbing layer side. The transmittance at the maximum wavelength (NIR absorbing layer: 1,100 nm) in the NIR region before and after the light resistance test was measured, and the light resistance was evaluated by the attenuation factor (A transmittance) of the transmittance.

From the results that the A transmittance could be reduced in each of Examples, it has been confirmed that an effect is exhibited against the photodegradation of the near-infrared absorber. As a result, it has been found that the resin composition of the present embodiment is excellent in preventing the photodegradation of the near-infrared absorber in the near-infrared absorbing layer.

From the fact that the particulate ultraviolet absorbers of Examples 1 to 3 are excellent in compression granulation property as compared with Comparative Example 1 and are excellent in feeding property as compared with Comparative Example 2, it has been found that the resin composition of the present embodiment exhibits good powder characteristics. Further, it has been found that the compounds of Examples 1 to 3 are excellent in ultraviolet absorbing characteristics and thus can be suitably used as an ultraviolet absorber.

This application claims priority based on Japanese Patent Application No. 2018-067807 filed on Mar. 30, 2018 and Japanese Patent Application No. 2018-067830 filed on Mar. 30, 2018, the entire disclosure of which is incorporated herein.

The invention claimed is:

1. A particulate ultraviolet absorber comprising:
a triazine-based compound,
wherein compressibility represented by [(D2−D1)/D2]× 100 is 5.0% or more and 40% or less, in a case where a loose bulk density is denoted by D1 and a tight bulk density is denoted by D2, which are measured under the following measurement condition:
(measurement condition)
a container having a diameter of 5 cm and a volume of 100 cm$^3$ is filled with the particulate ultraviolet absorber, the particulate ultraviolet absorber is leveled off without tapping, and then the loose bulk density (g/cm³) of the particulate ultraviolet absorber in the container is measured, and a container having a diameter of 5 cm and a volume of 100 cm³ is filled with the particulate ultraviolet absorber, the particulate ultraviolet absorber is, tapped from a height of 18 mm under a condition of 180 times of tapping by using a powder characteristics evaluation device and, leveled off, and then the tight bulk density (g/cm³) of the particulate ultraviolet absorber in the container is measured.

2. The particulate ultraviolet absorber according to claim 1,
wherein the triazine-based compound includes a compound represented by General Formula (I),

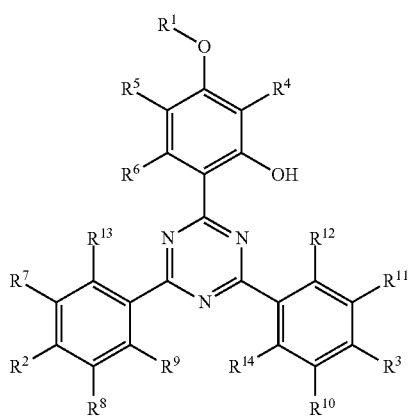

(I)

[in General Formula (I),
$R^1$ represents a linear or branched alkyl group having 1 to 20 carbon atoms, a cycloalkyl group having 3 to 20 carbon atoms, an aryl group having 6 to 20 carbon atoms, an alkylaryl group having 7 to 20 carbon atoms, an arylalkyl group having 7 to 20 carbon atoms, or an alkenyl group having 2 to 8 carbon atoms, which is substituted or unsubstituted, or a substituent represented by General Formula (II),
$R^2$ and $R^3$ each independently represent a hydrogen atom, a linear or branched alkyl group having 1 to 20 carbon atoms, which is substituted or unsubstituted, or —O—R, where R represents a linear or branched alkyl group having 1 to 20 carbon atoms, a cycloalkyl group having 3 to 20 carbon atoms, an aryl group having 6 to 20 carbon atoms, an alkylaryl group having 7 to 20 carbon atoms, or an arylalkyl group having 7 to 20 carbon atoms, which is substituted or unsubstituted,
$R^4$, $R^5$, $R^6$, $R^7$, $R^8$, $R^9$, $R^{10}$, $R^{11}$, and $R^{12}$ each independently represent a hydrogen atom, a halogen atom, or a linear or branched alkyl group having 1 to 8 carbon atoms or a linear or branched alkenyl group having 2 to 8 carbon atoms, which is substituted or unsubstituted, and $R^{13}$ and $R^{14}$ each independently represent a hydrogen atom or a hydroxy group, here, a methylene group in a linear or branched alkyl group represented by $R^1$, $R^2$, $R^3$, and R, which has 1 to 20 carbon atoms and is substituted or unsubstituted, and in a linear or branched alkyl group represented by $R^4$, $R^5$, $R^6$, $R^7$, $R^8$, $R^9$, $R^{10}$, $R^{11}$, and $R^{12}$, which has 1 to 8 carbon atoms and is substituted or unsubstituted, may be substituted with at least one or more structures selected from an oxygen atom, a sulfur atom, a carbon-carbon double bond, —CO—, —CO—O—, —OC—O—, —CO—NH—, —NH—CO—, —CR$^{O1}$=N—, and —N=CR$^{O2}$—, and $R^{O1}$ and $R^{O2}$ in the structures each independently represent a linear or branched alkyl group having 1 to 8 carbon atoms] and

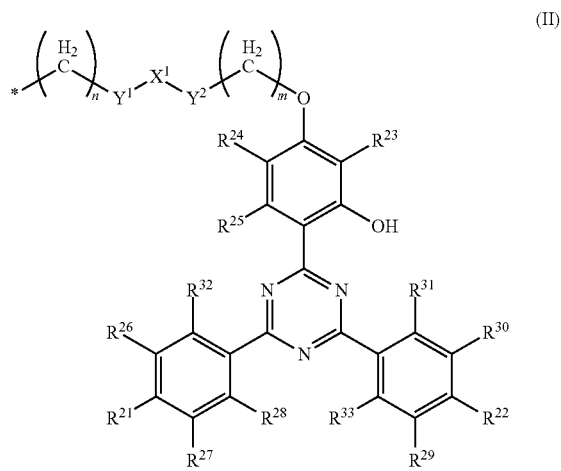

(II)

[in General Formula (II),
$R^{21}$ and $R^{22}$ each independently represent a hydrogen atom, a linear or branched alkyl group having 1 to 20 carbon atoms, which is substituted or unsubstituted, or —O—R, where R represents a linear or branched alkyl group having 1 to 20 carbon atoms, a cycloalkyl group having 3 to 20 carbon atoms, an aryl group having 6 to 20 carbon atoms, an alkylaryl group having 7 to 20 carbon atoms, or an arylalkyl group having 7 to 20 carbon atoms, which is substituted or unsubstituted,
$R^{23}$, $R^{24}$, $R^{25}$, $R^{26}$, $R^{27}$, $R^{28}$, $R^{29}$, $R^{30}$, and $R^{31}$ each independently represent a hydrogen atom, a halogen atom, or a linear or branched alkyl group having 1 to 8 carbon atoms or a linear or branched alkenyl group having 2 to 8 carbon atoms, which is substituted or unsubstituted,
$R^{32}$ and $R^{33}$ each independently represent a hydrogen atom or a hydroxy group,
$X^1$ represents a linear or branched alkylene group having 8 or more and 30 or fewer carbon atoms, which is substituted or unsubstituted,
$Y^1$ and $Y^2$ each independently represent —CO—O—, —O—CO—, -L¹-, —O-L¹O—, —O-L¹-, -L¹-O—CO—, -L¹-CO—O—, —CO—CH=CH—, —CH=CH—CO—, —CH=CH—CO—O—, —CH=CH—O—CO—, and —CO—O—CH=CH—,
L¹ is a linear or branched alkylene group having 1 to 8 carbon atoms,
m and n each independently represent an integer of 0 to 8, and
* represents a bond with an oxygen atom linked to $R^1$ in Formula (I),
here, a methylene group in a linear or branched alkyl group represented by $R^{21}$, $R^{22}$, and R, which has 1 to 20 carbon atoms and is substituted or unsubstituted, in a linear or branched alkyl group represented by $R^{23}$, $R^{24}$, $R^{25}$, $R^{26}$, $R^{27}$, $R^{28}$, $R^{29}$, $R^{30}$, and $R^{31}$, which has 1 to 8 carbon atoms and is substituted or unsubstituted, and in a linear or branched alkylene group represented by $X^1$, which has 8 to 30 carbon atoms, may be substituted with at least one or more structures selected from an oxygen atom, a sulfur atom, a carbon-carbon double bond, —CO—, —CO—O—, —OC—O—, —CO—NH—, —NH—CO—, —$CR^{O3}$=N—, and —N=$CR^{O4}$—, and $R^{O3}$ and $R^{O4}$ each independently represent a linear or branched alkyl group having 1 to 8 carbon atoms].

3. The particulate ultraviolet absorber according to claim 1, wherein the triazine-based compound includes a compound represented by General Formula (A),

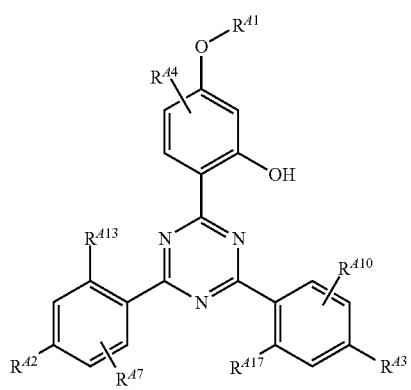
(A)

(in General Formula (A), $R^{A1}$ represents a linear or branched alkyl group having 1 to 12 carbon atoms, a cycloalkyl group having 3 to 8 carbon atoms, an linear or branched alkenyl group having 3 to 8 carbon atoms, an aryl group having 6 to 18 carbon atoms, an alkylaryl group having 7 to 18 carbon atoms, or an arylalkyl group having 7 to 18 carbon atoms, $R^{A2}$ and $R^{A3}$ may be the same or different from each other and represent a hydrogen atom, a linear or branched alkyl group having 1 to 12 carbon atoms, or a linear or branched alkoxy group having 1 to 12 carbon atoms, $R^{A4}$, $R^{A7}$, and $R^{A10}$ may be the same or different from each other and represent a hydrogen atom, a linear or branched alkyl group having 1 to 8 carbon atoms, or a linear or branched alkenyl group having 3 to 8 carbon atoms, and $R^{A13}$ and $R^{A17}$ may be the same or different from each other and represent a hydrogen atom or a hydroxy group, here, a methylene group in a linear or branched alkyl group represented by $R^{A1}$, $R^{A2}$, and $R^{A3}$, which has 1 to 12 carbon atoms, and a linear or branched alkoxy group represented by $R^{A2}$ and $R^{A3}$, which has 1 to 12 carbon atoms, may be substituted with at least one or more structures selected from an oxygen atom, a sulfur atom, a carbon-carbon double bond, —CO—, —CO—O—, —OC—O—, —CO—NH—, —NH—CO—, —$CR^{O5}$=N—, and —N=$CR^{O6}$—, and $R^{O5}$ and $R^{O6}$ in the structures each independently represent a linear or branched alkyl group having 1 to 8 carbon atoms).

4. The particulate ultraviolet absorber according to claim 1, wherein the triazine-based compound includes one or two or more compounds represented by any of Compound No. 1A to Compound No. 8A, Compound No. 1A
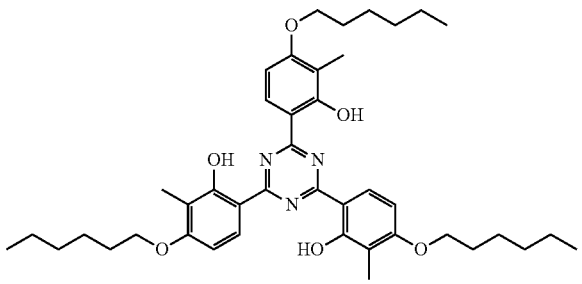

Compound No. 2A
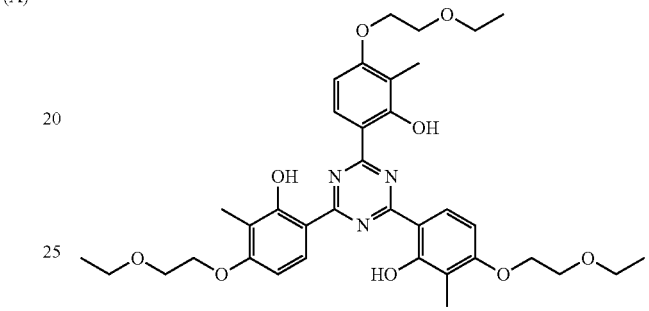

Compound No. 3A
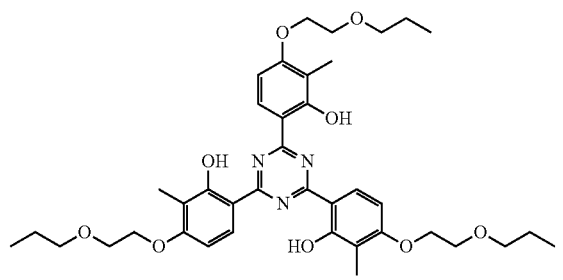

Compound No. 4A
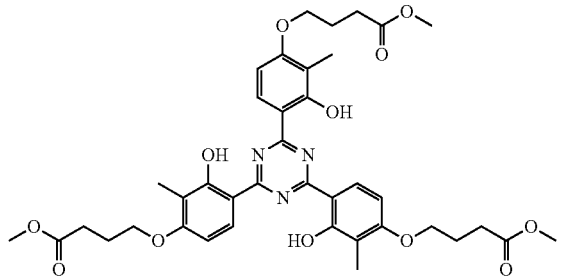

Compound No. 5A
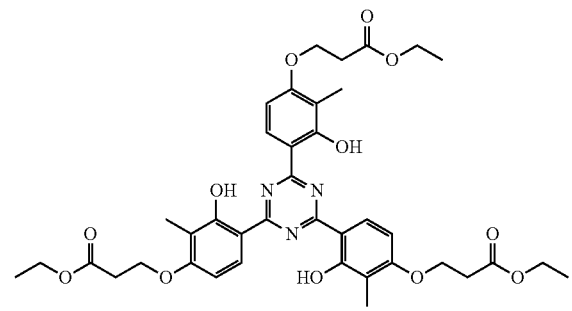

-continued

Compound No. 6A

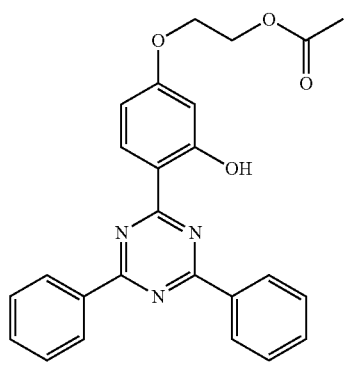

Compound No. 7A

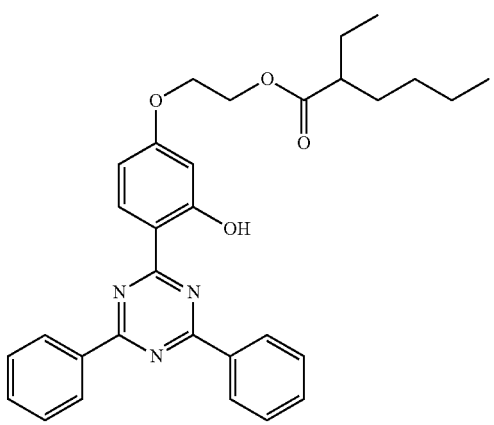

Compound No. 8A

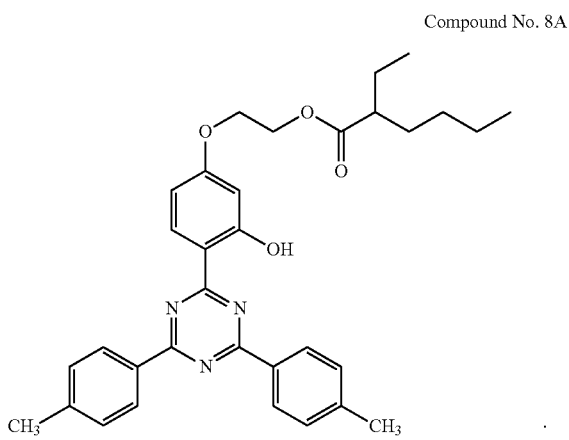

5. The particulate ultraviolet absorber according to claim 1, wherein the triazine-based compound includes a compound represented by General Formula (B),

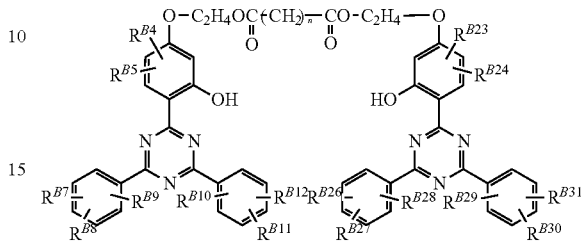

(B)

(in General Formula (B), $R^{B4}$, $R^{B5}$, $R^{B7}$ to $R^{B9}$, $R^{B10}$ to $R^{B12}$, $R^{B23}$, $R^{B24}$, $R^{B26}$ to $R^{B28}$, and $R^{B29}$ to $R^{B31}$ each independently represent a hydrogen atom, a hydroxy group, a halogen atom, or an alkyl group having 1 to 20 carbon atoms, an alkenyl group having 2 to 20 carbon atoms, an alkoxy group having 1 to 20 carbon atoms, or an aryl group having 6 to 20 carbon atoms, and n represents an integer of 8 to 14, here, a para-position of two of three benzene rings linked to a triazine ring represents a hydrogen atom, an alkyl group having 1 to 20 carbon atoms, or an alkoxy group having 1 to 20 carbon atoms, and one of ortho-positions represents a hydrogen atom or a hydroxy group).

6. The particulate ultraviolet absorber according to claim 5, wherein the triazine-based compound includes one or two or more compounds represented by any of Compound No. 1B to Compound No. 4B, Compound No. 1B

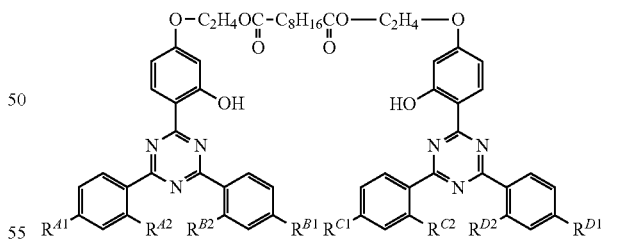

Compound No. 2B

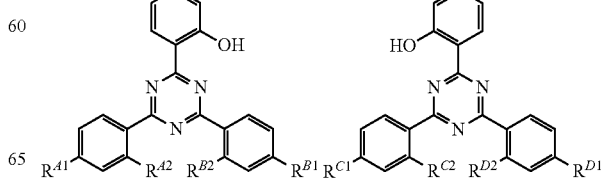

-continued

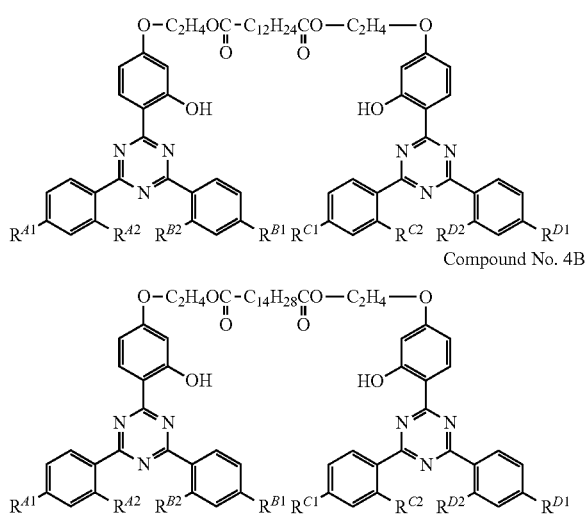

Compound No. 3B

Compound No. 4B (in Compound No. 1B to Compound No. 4B, $R^{A1}$, $R^{A2}$, $R^{B1}$, $R^{B2}$, $R^{C1}$, $R^{C2}$, $R^{D1}$, and $R^{D2}$ may be the same or different from each other and represent a hydrogen atom, a linear or branched alkyl group having 1 to 4 carbon atoms, or a linear or branched alkoxy group having 1 to 4 carbon atoms).

7. The particulate ultraviolet absorber according to claim 1, wherein the loose bulk density D1 is 0.20 g/cm$^3$ or more and 0.70 g/cm$^3$ or less.

8. The particulate ultraviolet absorber according to claim 1, wherein the tight bulk density D2 is 0.40 g/cm$^3$ or more and 0.90 g/cm$^3$ or less.

9. The particulate ultraviolet absorber according to claim 1, wherein the triazine-based compound has a maximum peak within a range in which a diffraction angle 2θ is 5.00° or more and 6.50° or less in a powder X-ray diffraction analysis pattern.

10. The particulate ultraviolet absorber according to claim 9, wherein a half-width of the maximum peak of the triazine-based compound is 0.05° or more and 0.20° or less.

11. The particulate ultraviolet absorber according to claim 9, wherein a diffraction peak having the relative intensity of 30 or more and 60 or less is not present within a range in which a diffraction angle 2θ is 3.0° or more and 45.0° or less, in a case where a relative intensity of the maximum peak of the triazine-based compound is set to 100.

12. The particulate ultraviolet absorber according to claim 9, wherein a diffraction peak having the relative intensity of 1 or more and 5 or less is not present within a range in which a diffraction angle 2θ is more than 45.0° and 60.0° or less, in a case where a relative intensity of the maximum peak of the triazine-based compound is set to 100.

13. A resin composition comprising:
the particulate ultraviolet absorber according to claim 1.

14. The resin composition according to claim 13, wherein the resin composition contains a synthetic resin.

* * * * *

UNITED STATES PATENT AND TRADEMARK OFFICE
CERTIFICATE OF CORRECTION

| | | |
|---|---|---|
| PATENT NO. | : 11,780,990 B2 | Page 1 of 1 |
| APPLICATION NO. | : 17/043074 | |
| DATED | : October 10, 2023 | |
| INVENTOR(S) | : Y. Ishima et al. | |

It is certified that error appears in the above-identified patent and that said Letters Patent is hereby corrected as shown below:

On the Title Page

Item (56), Line 4 under OTHER PUBLICATIONS, please insert -- International Search Report issued in International Patent Application No. PCT/JP2019/012517, dated May 7, 2019, along with an English translation thereof --

Signed and Sealed this
Nineteenth Day of March, 2024

Katherine Kelly Vidal
*Director of the United States Patent and Trademark Office*